United States Patent [19]

Spector et al.

[11] Patent Number: 5,321,138

[45] Date of Patent: Jun. 14, 1994

[54] COMPOUNDS HAVING GLUTATHIONE PEROXIDASE ACTIVITY AND USE THEREOF

[75] Inventors: Abraham Spector, New York, N.Y.; Stephen R. Wilson, Chatham; Paul A. Zucker, Maplewood, both of N.J.

[73] Assignees: The Trustees of Columbia University in the City of New York; New York University, both of New York, N.Y.

[21] Appl. No.: 692,931

[22] Filed: Apr. 29, 1991

Related U.S. Application Data

[63] Continuation-in-part of Ser. No. 383,189, Jul. 19, 1989, Pat. No. 5,128,365.

[51] Int. Cl.⁵ .................... C07C 37/02; A01K 31/095
[52] U.S. Cl. .................................. 546/224; 548/540; 548/575; 548/524; 562/899
[58] Field of Search ............... 562/899; 548/575, 540, 548/524; 546/224; 514/706, 428, 423, 352, 422

[56] References Cited

U.S. PATENT DOCUMENTS 4,873,350 10/1989 Welter ................................ 549/436

OTHER PUBLICATIONS

Wilson et al., JACS 111, 5936 (1989).

Primary Examiner—Robert Gerstl
Attorney, Agent, or Firm—John P. White

[57] ABSTRACT

The present invention provides compounds having glutathione peroxidase activity and, therefore, are effective glutathione peroxidase replacements. These compounds are useful as drugs for the prevention of cataracts and as anti-oxidants for $H_2O_2$ and other peroxides. The present invention also provides methods and pharmaceutical compositions of the compound.

27 Claims, 15 Drawing Sheets

* NORMALIZED BASED ON

COMPOUNDS HAVING GLUTATHIONE PEROXIDASE ACTIVITY AND USE THEREOF

This invention was made with support under Grant Numbers NEI EY00423 and GM-29259 from the National Institutes of Health, U.S. Department of Health and Human Services. Accordingly, the U.S. Government has certain rights in the invention.

BACKGROUND OF THE INVENTION

This application is a continuation-in-part of U.S. Ser. No. 07/383,189, filed Jul. 19, 1989, now U.S. Pat. No. 5,128,765, the contents of which are hereby incorporated by reference into this application.

Throughout this application, various publications are referenced by Arabic numerals within parentheses. Full citations for these publications may be found at the end of the specification immediately preceding the claims. The disclosures of these publications in their entirety are hereby incorporated by reference into this application in order to more fully describe the state of the art as known to those skilled therein as of the date of the invention described and claimed herein.

Glutathione peroxidase is a selenoenzyme composed of four identical subunits of 21,000 Da which catalyzes the reduction of $H_2O_2$ and other hydroperoxides (1, 2). In many tissues, such as the lens of the eye, glutathione peroxidase is the major defense against hydroperoxides (3). Researchers have implicated hydrogen peroxide damage as a major cause in the formation of cataracts. Glutathione 1 has the formula $H_2N\gamma Glu\text{-}Cys\text{-}Gly\text{-}OH$ and is utilized as a cofactor, supplying the electrons for the reductive reaction:

$$ROOH + 2GSH \rightarrow ROH + H_2O + GSSG \quad (eq\ 1)$$

Other compounds can also be utilized as cofactors, e.g., ascorbic acid, cysteine, cystamine, dithiotheitol, glutathione, and mercaptoethanol.

The X-ray crystal structure of GSH peroxidase has been determined with 0.2-nm resolution. The results from such analyses, as well as biochemical data have been used to develop a reaction mechanism for the reaction (2). The mechanism in FIG. 1 shows the selenium atom going from a selenol (E—Se—H) to a selenenic acid (E—SeOH). In the presence of high concentrations of peroxide, it can be further oxidized to a sileninic acid (E—SeOOH). Thus, FIG. 1 illustrates the two-step reduction of selenic acid utilizes 2 mol of GSH/mol of enzyme.

Earlier work, in this laboratory, directed toward the development of compounds having GSH peroxidase activity, met with only limited success (4). This work was based on the design of small molecules which would mimic the structure of the active site of the enzyme containing the essential selenocystine residue. The most active compound produced in this study, 2, proved to be only 0.033 as active as the Ebselen compound, 3, the most active compound previously known (5).

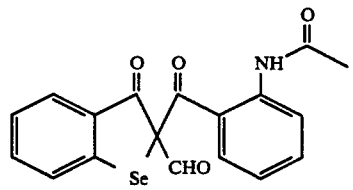

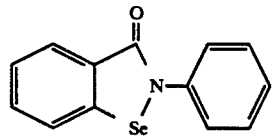

Recently, a report by Reich and Jasperse (6) described the oxidation-reduction chemistry of 4 (FIG. 2). The results of this study suggest that two mechanistic pathways, A and B, are possible for the catalysis of 4 of the reduction of hydroperoxides by thiols. The following observations were especially interesting from a mechanistic viewpoint:

(1) under acid catalysis, the selenamide, 4, equilibrates with seleninamide, 8, and diselenide, 7. These compounds are produced by disproportionation of the selenenamide, 4;

(2) oxidation of 6 with MCPBA first gave the diselenide, 7, and then the seleninamide 8;

(3) oxidation of 4 produced the seleninamide, 8, and the oxidation rate was faster than the oxidation rate of the diselenide;

(4) under weakly acidic conditions, treatment of 4 with thiols gave the selenosulfide 5 and disulfide; and (5) neither the selenosulfide 5 nor diselenide 7 reacted with thiol under neutral conditions. However, upon addition of a strong amine base (DBU), both gave the selenolate and disulfide.

These results suggest some guidelines for the construction of molecules showing GSH activity:

(1) more easily available diselenides would function as effectively as the more difficult to construct cyclic compounds in the production of the catalytically active species (observations 1–4 above); and (2) inclusion in the molecule of a strongly basic group proximal to the active selenium atom is desirable as it would be expected to catalyze the reaction of thiols with the intermediate diselenide and selenosulfide. Presumably, the base functions to provide a source of nucleophilic thiolate anion (observation 5 above).

With these guidelines in mind, we chose as compounds for study, tertiary amines of the type 13 (FIG. 3). The use of tertiary amines seemed preferable to that of primary or secondary amines since intermediate 10 and 14 are not stable compounds and are thus activated toward nucleophilic attack by thiol at the selenium atom.

FIG. 4 illustrates the competition between hydrogen peroxide and oxygen for selenol (RSeH). A free radical trapper can block the reduction of the selenol by oxygen, and thereby prevent the depletion of the cofactors necessary to maintain the compound in its selenol form. The use of a free radical trapper allows the reduction of the peroxide while preventing the oxidation of the selenol by oxygen.

Free radical trappers are compounds that trap free radicals by binding to the free radicals. Examples of free radical trappers include 2,2,6,6-tetramethylpiperidine-1- oxyl and 2,2,5,5,-tetramethyl-3-pyrroline-1-oxyl-3-carboxylic acid. The free radical trapper can either be mixed with the selenol or attached directly to the selenol. In addition to preventing the oxidation of the selenol by oxygen, the use of a free radical trapper reduces the toxicity of the selenol. DNA damage to lens epithelial cells is essentially eliminated when the selenol is combined with a free radical trapper. Thus, the use of a free radical trapper with the selenol allows the reduction of peroxides in the eye without damage to the lens epithelial cells.

Superoxides and hydroxyl radicals are also present during oxidative stress and may also arise as a result of reactions involving peroxides. The combination of glutathione peroxidase mimics and free radical traps eliminates peroxide as well as these radicals.

SUMMARY OF THE INVENTION

The present invention provides a compound having the structure:

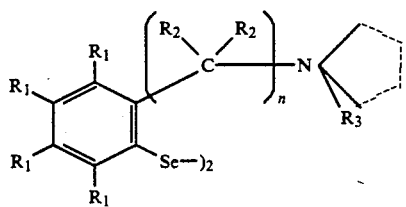

wherein n is an integer between 1 and 30; wherein each $R_1$ may be the same or different and represents an electron-donating group, an electron-withdrawing group, a lower alkyl group, a lower alkyl group containing one or more hydroxyl groups, or hydrogen; wherein each $R_2$ may be the same or different and represents a lower alkyl group, a lower alkyl group containing one or more hydroxyl groups, a hydroxyl group, an alcohol group, or hydrogen; wherein $R_3$ represents a hydrogen atom or a lower alkyl group which may be present or absent, which if present results in a positive charge on N; and wherein the dashed lines represent carbon-carbon bonds which may be present or absent.

The present invention also concerns a compound having the structure:

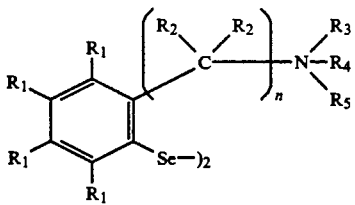

wherein n is an integer between 1 and 30; wherein each $R_1$ may be the same or different and represents an electron-donating group, an electron-withdrawing group, a lower alkyl group, a lower alkyl group containing one or more hydroxyl groups, or hydrogen; wherein each $R_2$ may be the same or different and represents a lower alkyl group, a lower alkyl group containing one or more hydroxyl groups, a hydroxyl group, an alcohol group, or hydrogen; wherein $R_3$ represents a lower alkyl group or hydrogen; wherein $R_4$ represents a lower alkyl group or hydrogen; and wherein $R_5$ represents a hydrogen atom or a lower alkyl group which may be present or absent, which if present results in a positive charge on N.

The present invention also concerns a method of reducing $H_2O_2$ and/or other peroxides which comprises contacting $H_2O_2$ and/or other peroxides with a suitable amount of any of the compounds of the invention effective to reduce $H_2O_2$ and/or other peroxides.

Additionally, the invention provides a method of treating a peroxide-induced condition in a subject which comprises administering to the subject an amount of any of the compounds of the invention effective to reduce peroxide in a subject and thereby treat the peroxide-induced condition.

Further, the invention provides a pharmaceutical composition which comprises an amount of any of the compounds of the invention effective to reduce peroxide in a subject with a peroxide-induced condition and a pharmaceutically acceptable carrier.

The invention also provides a method of treating a peroxide- or free radical-induced condition in a subject which comprises administering to the subject an amount of a composition comprising (1) a compound having the structure:

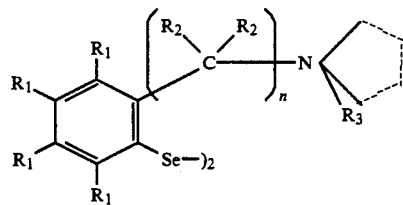

wherein n is an integer between 1 and 30; wherein each $R_1$ may be the same or different and represents an electron-donating group, an electron-withdrawing group, a lower alkyl group, a lower alkyl group containing one or more hydroxyl groups, or hydrogen; wherein each $R_2$ may be the same or different and represents a lower alkyl group, a lower alkyl group containing one or more hydroxyl groups, a hydroxyl group, an alcohol group, or hydrogen; wherein $R_3$ represents a hydrogen atom or a lower alkyl group which may be present or absent, which if present results in a positive charge on N; and wherein the dashed lines represent carbon-carbon bonds which may be present or absent, and (2) a free radical trapper, effective to reduce peroxide or free radicals in the subject and thereby treat the peroxide- or free radical-induced condition.

BRIEF DESCRIPTION OF THE FIGURES

FIG. 6 illustrates the synthesis of:

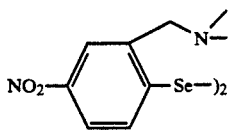

Figure 7:
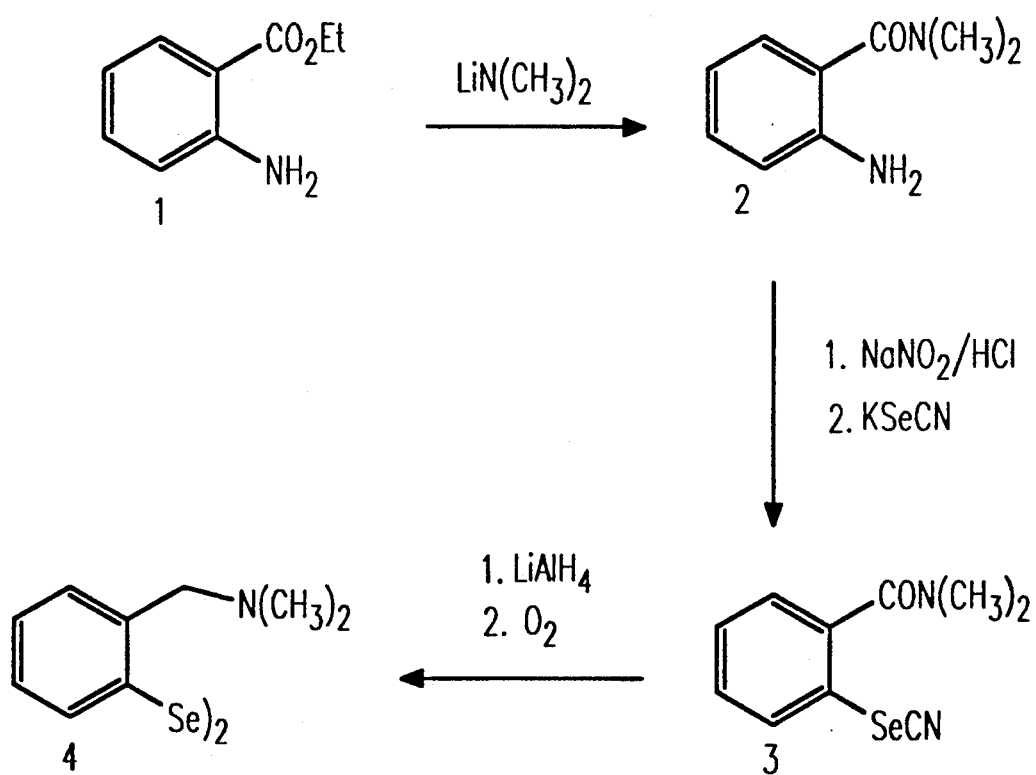

FIG. 7 illustrates one method of synthesis for:

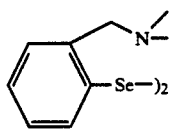

FIG. 8 shows the absorption spectrum of the mimic in the oxidized form (8(a)), reduced by GSH (8(b)), and oxidized by air (8(c)). The Figure also shows the mimic and Tempo with mimic in the oxidized form (8(d)), reduced by GSH (8(e)), and exposed to air (8(f)).

Figure 9:
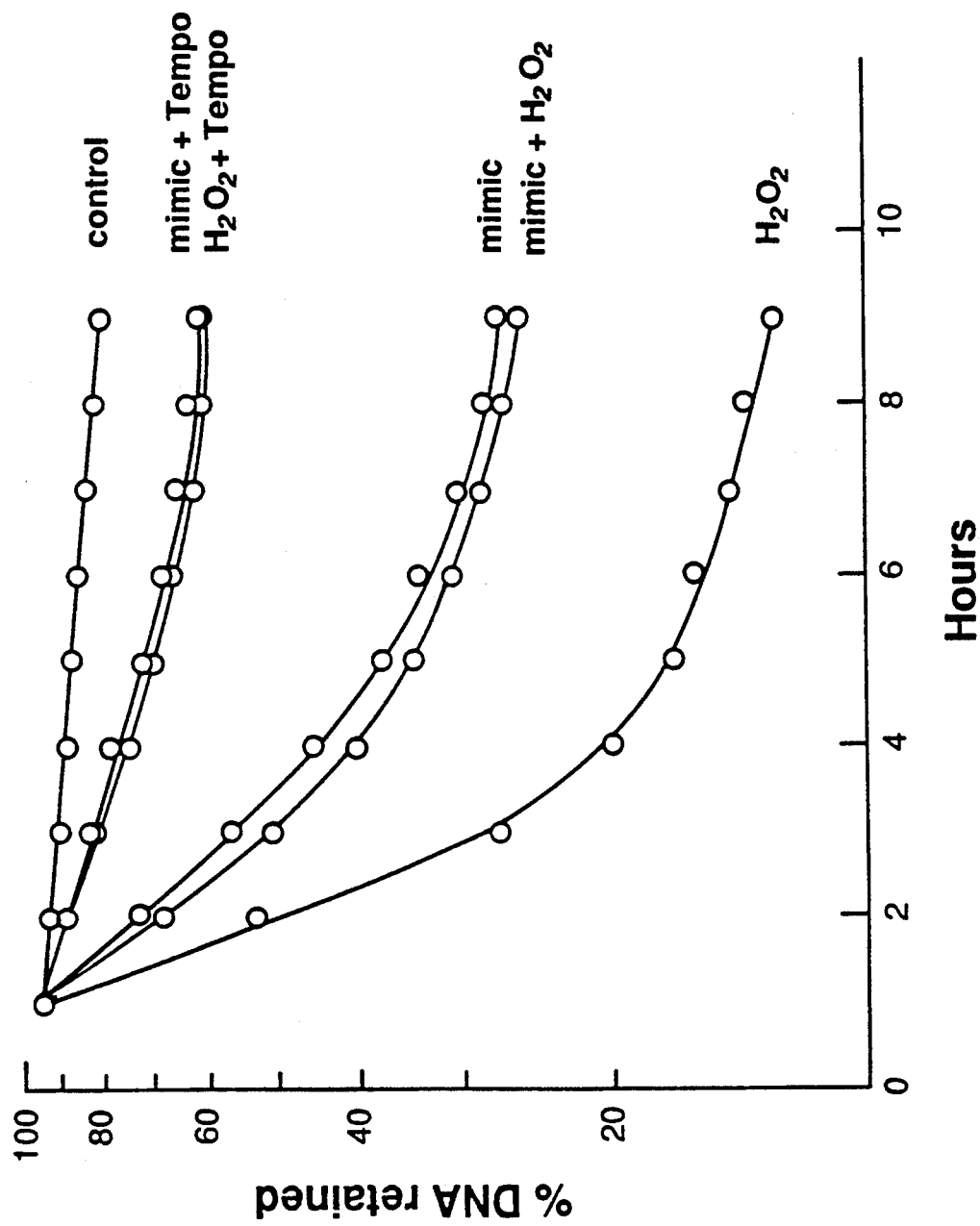

FIG. 9 shows DNA damage to lens epithelial cells for various combinations of mimic, $H_2O_2$, and Tempo.

Figure 10:
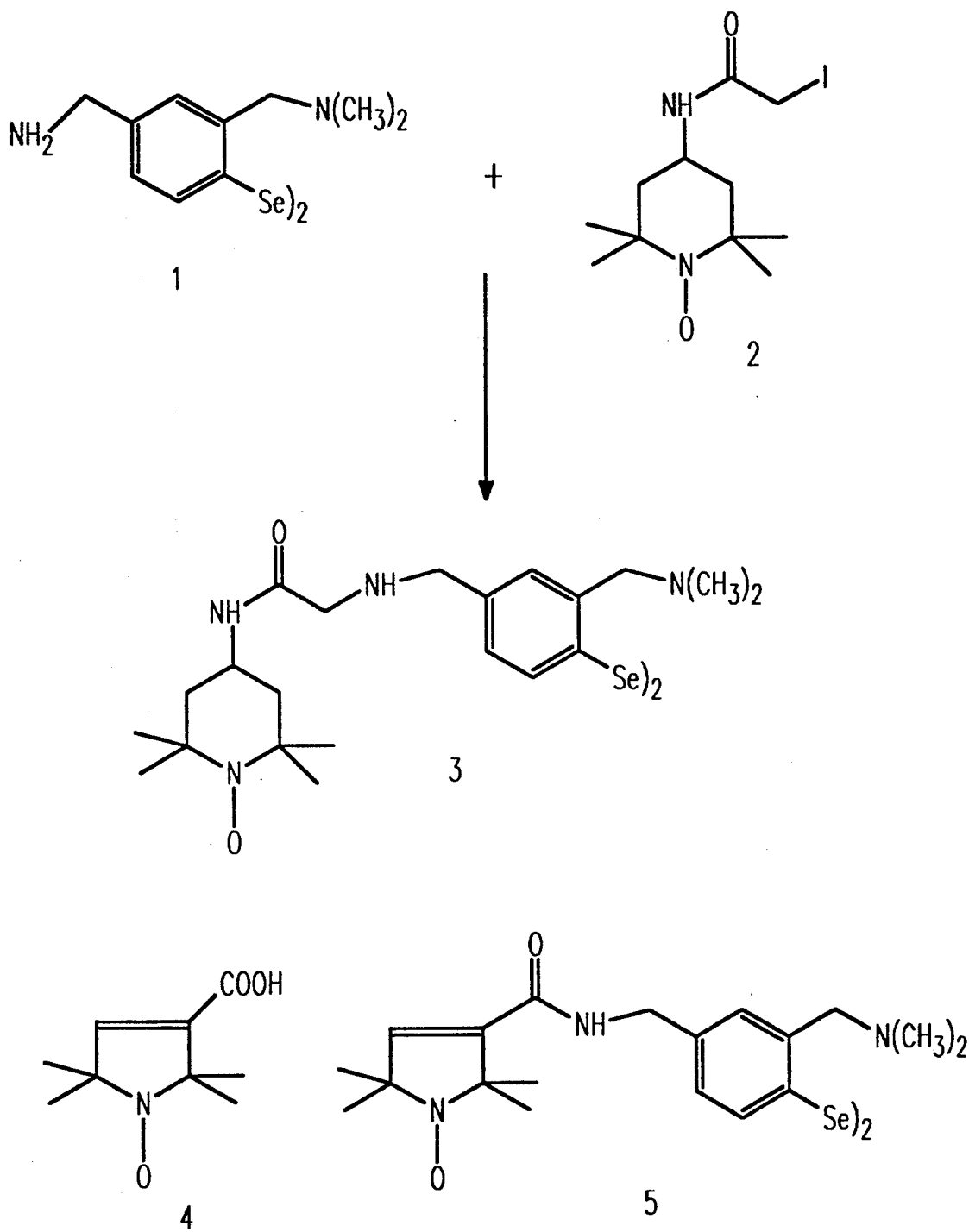

FIG. 10 shows a reaction scheme for attaching a free radical trapper to the mimic.

DETAILED DESCRIPTION OF THE INVENTION

The present invention provides a compound having the structure:

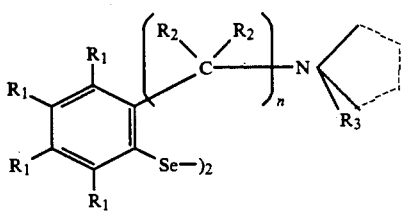

wherein n is an integer between 1 and 30; wherein each $R_1$ may be the same or different and represents an electron-donating group, an electron-withdrawing group, a lower alkyl group, a lower alkyl group, containing one or more hydroxyl groups, or hydrogen; wherein each $R_2$ may be the same or different and represents a lower alkyl group, a lower alkyl group containing one or more hydroxyl groups, a hydroxyl group, an alcohol group, or hydrogen; wherein $R_3$ represents a hydrogen atom or a lower alkyl group which may be present or absent, which if present results in a positive charge on N; and wherein the dashed lines represent carbon-carbon bonds which may be present or absent.

As used herein, an electron-donating group is a group of atoms, in an organic molecule, which gives electrons to the remaining atoms in the molecule. Examples of electron-donating groups include, but are not limited to, —$CH_3$, —OH, and $CH_3O$. These groups produce an inductive or a mesomeric effect.

As used herein, an electron-withdrawing group is a group of atoms, in an organic molecule, which gives electrons to the remaining atoms in the molecule. Examples of electron-withdrawing groups include, but are not limited to, —$NO_2$, —$SO_3H$, and —CN. These groups produce an inductive or mesomeric effect.

Any of $R_1$ or $R_2$ may be a lower alkyl group containing one or more hydroxyl groups. This group could be attached to increase the water solubility of the compound. Other groups, e.g. an alcohol group, can also be attached to increase water solubility.

Further, the invention provides a compound having the structure:

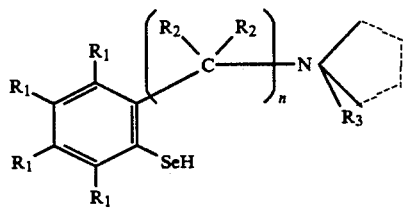

wherein n is an integer between 1 and 30; wherein each $R_1$ may be the same or different and represents an electron-donating group, an electron-withdrawing group, a lower alkyl group, a lower alkyl group containing one or more hydroxyl groups, or hydrogen; wherein each $R_2$ may be the same or different and represents a lower alkyl group, a lower alkyl group containing one or more hydroxyl groups, a hydroxyl group, an alcohol group, or hydrogen; wherein $R_3$ represents a hydrogen atom or a lower alkyl group which may be present or absent, which if present results in a positive charge on N; and wherein the dashed lines represent carbon-carbon bonds which may be present or absent.

The invention also provides a compound having the structure:

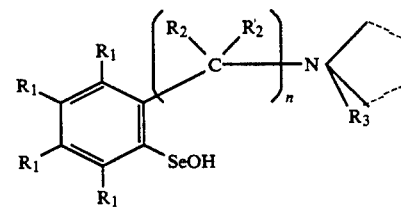

wherein n is an integer between 1 and 30; wherein each $R_1$ may be the same or different and represents an electron-donating group, an electron-withdrawing group, a lower alkyl group, a lower alkyl group containing one or more hydroxyl groups, or hydrogen; wherein each $R_2$ may be the same or different and represents a lower alkyl group, a lower alkyl group containing one or more hydroxyl groups, a hydroxyl group, an alcohol group, or hydrogen; wherein $R_3$ represents a hydrogen atom or a lower alkyl group which may be present or absent, which if present results in a positive charge on N; and wherein the dashed lines represent carbon-carbon bonds which may be present or absent.

The invention provides the above described compounds wherein n is preferably from 1 to 6.

The compounds described herein are synthetic mimics of glutathione peroxidase and therefore are effective glutathione replacements. These compounds are useful as drugs for the prevention of cataracts, especially maturity onset cataract development. Further, these compounds are useful as anti-oxidants for $H_2O_2$ and other peroxides.

Moreover, when using these compounds as drugs, glutathione or derivatives thereof may be added to the compounds of the invention, functioning as cofactors which supply the electrons for the reduction of the peroxide. Other compounds can also be utilized as co-factors., e.g., ascorbic acid, cystsine, cystamine, dithiothreitol, glutathione, and mercaptoethanol.

In the above described compounds, one or more $R_1$ may be a thiol or thioester. Further, one or more $R_1$ may be —SH or —S—$CH_3$.

Additionally, the invention provides a compound having the structure:

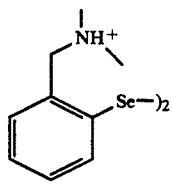

including a salt, e.g. a chloride salt, of the compound.

The invention also concerns a compound having the structure:

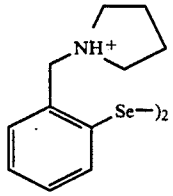

including salt, e.g., a chloride salt, of the compound.

The invention further provides a compound having a structure:

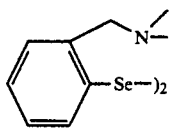

The invention also provides a compound having a structure:

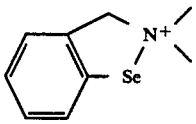

The invention still further provides a compound having a structure:

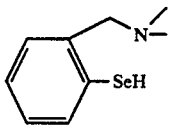

The invention also provides a compound having a structure:

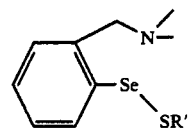

Further, the invention provides a compound having a structure:

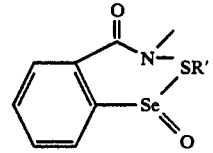

The present invention provides a compound having a structure:

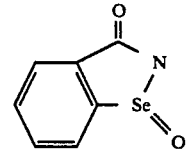

The present invention additionally provides compound having a structure:

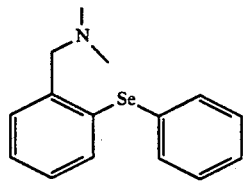

The present invention additionally provides compound having a structure:

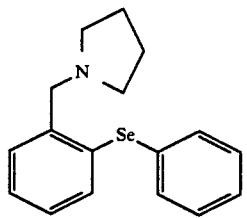

The present invention also concerns a method of reducing $H_2O_2$ and/or other peroxides which comprises contacting $H_2O_2$ and/or other peroxides with an amount of a compound having the structure:

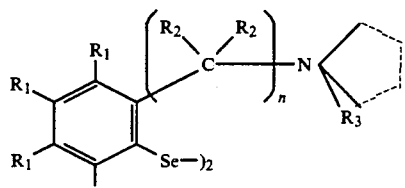

effective to reduce H₂O₂ and/or other peroxides.

The present invention also concerns a method of reducing H₂O₂ and/or other peroxides which comprises contacting H₂O₂ and/or other peroxides with an amount of a compound having the structure:

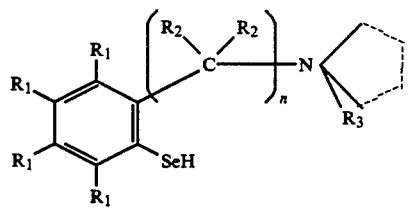

effective to reduce H₂O₂ and/or other peroxides.

The present invention also concerns a method of reducing H₂O₂ and/or other peroxides which comprises contacting H₂O₂ and/or other peroxides with an amount of a compound having the structure:

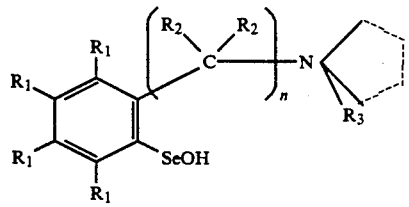

effective to reduce H₂O₂ and/or other peroxides.

Further, the invention provides a method of treating a peroxide-induced condition in a subject, e.g. a human subject, which comprises administering, e.g. by topical, oral, intravenous, intraperitoneal, intramusculer, intradermal, or subcutaneous administration, to the subject an amount of a compound having the structure:

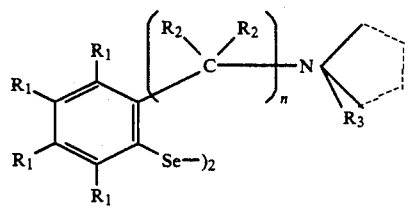

effective to reduce peroxide in the subject and thereby treat the peroxide-induced condition. It is worthy to point out at this time that the administration of the compound to the subject may be effected by means other than those listed herein. Further, the peroxide-induced condition may involve cataracts, inflammation of a tissue, eschemia, an allergic reaction, or pathology caused by oxidative stress. Where the peroxide-induced condition involves cataracts, administration is effected by, but is not limited to, topical contact to the surface of an eye.

The present invention also concerns a method of reducing H₂O₂ and/or other peroxides which comprises contacting H₂O₂ and/or other peroxides with a suitable amount of any of the compounds of the invention effective to reduce H₂O₂ and/or other peroxides.

Additionally, the invention provides a method of treating a peroxide-induced condition in a subject which comprises administering to the subject an amount of any of the compounds of the invention effective to reduce peroxide in a subject and thereby treat the peroxide-induced condition.

The present invention also concerns a compound having the structure:

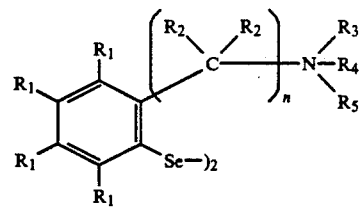

wherein n is an integer between 1 and 30; wherein each $R_1$ may be the same or different and represents an electron-donating group, an electron-withdrawing group, a lower alkyl group, a lower alkyl group containing one or more hydroxyl groups, or hydrogen; wherein each $R_2$ may be the same or different and represents a lower alkyl group, a lower alkyl group containing one or more hydroxyl groups, a hydroxyl group, an alcohol group, or hydrogen; wherein $R_3$ represents a lower alkyl group or hydrogen; wherein $R_4$ represents a lower alkyl group or hydrogen; and wherein $R_5$ represents a hydrogen atom or a lower alkyl group which may be present or absent, which if present results in a positive charge on N.

In the above-described compound, n is preferably from 1 to 6. Further, one or more $R_1$ may be a thiol or thioester, and one or more $R_1$ may be —SH or —S—CH₃.

The invention additionally provides a method of reducing H₂O₂ and/or other peroxides which comprises contacting H₂O₂ and/or other peroxides with an amount of the compound having the structure:

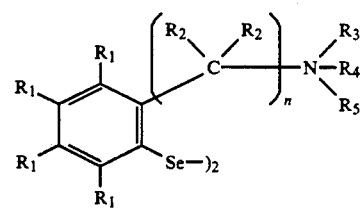

effective to reduce H₂O₂ and/or other peroxides.

Further, the invention provides a method of treating a peroxide-induced condition in a subject, e.g. a human being, which comprises administering, e.g. by topical, oral, intravenous, intraperitoneal, intramuscular, intradermal, or subcutaneous administration, to the subject an amount of the compound having the structure:

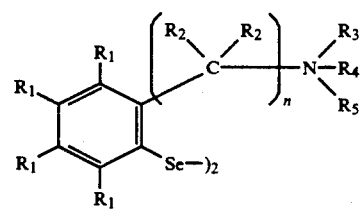

effective to reduce peroxide in the subject and thereby treat the peroxide-induced condition.

In this method the peroxide-induced condition may involve cataracts, in such cases, administration may be effected, but is not necessarily limited to, topical contact on the surface of the eye. Further, in this method, the peroxide-induced condition may involve inflammation of a tissue, eschemia, an allergic reaction, or pathology caused by oxidative stress.

Additionally, the invention provides a method of reducing $H_2O_2$ and/or other peroxides which comprises contacting $H_2O_2$ and or other peroxides with an amount of the compounds previously described which are derived from compounds having the structure:

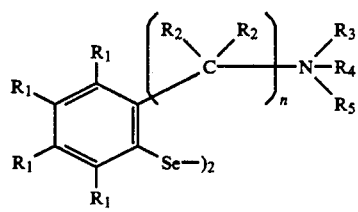

effective to reduce $H_2O_2$ and/or other peroxides.

Further, the present invention also provides a method of treating a peroxide-induced condition in a subject which comprises administering to the subject an amount of the compounds previously described which are derived from the compound having the structure:

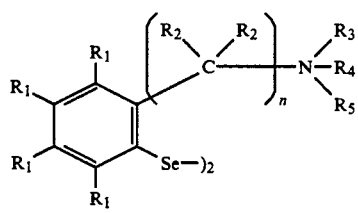

effective to reduce peroxides in a subject and thereby treat the peroxide-induced condition.

The present invention additionally provides a method of reducing $H_2O_2$ which comprises contacting $H_2O_2$ with an amount of a compound having the structure:

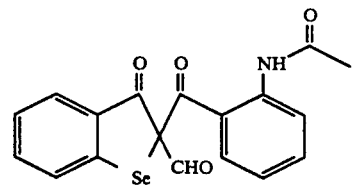

effective to reduce $H_2O_2$.

The invention further provides a method of reducing $H_2O_2$ which comprises contacting $H_2O_2$ with an amount of a compound having the structure:

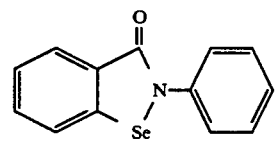

effective to reduce $H_2O_2$.

Moreover, the invention concerns a method of reducing $H_2O_2$ which comprises contacting $H_2O_2$ with an amount of a compound having the structure:

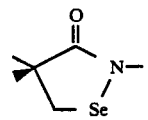

effective to reduce $H_2O_2$.

The present invention also concerns a method of reducing $H_2O_2$ which comprises contacting $H_2O_2$ with an amount of a compound having the structure:

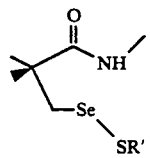

effective to reduce $H_2O_2$.

The present invention provides a method of reducing $H_2O_2$ which comprises contacting $H_2O_2$ with an amount of a compound having the structure:

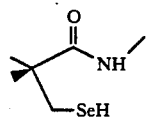

effective to reduce $H_2O_2$.

Another provision concerns a method of reducing $H_2O_2$ which comprises contacting $H_2O_2$ with an amount of a compound having the structure:

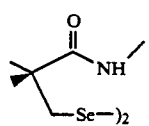

effective to reduce $H_2O_2$.

Further, the invention provides method of reducing $H_2O_2$ which comprises contacting $H_2O_2$ with an amount of a compound having the structure:

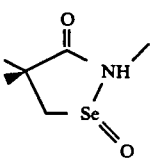

effective to reduce $H_2O_2$.

Further still the invention provides a method of reducing $H_2O_2$ which comprises contacting $H_2O_2$ with an amount of a compound having the structure:

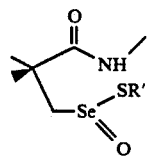

effective to reduce $H_2O_2$.

Additionally, the invention concerns a method of reducing $H_2O_2$ which comprises contacting $H_2O_2$ with an amount of a compound having the structure:

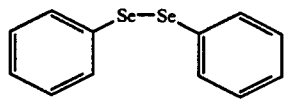

effective to reduce $H_2O_2$.

The invention also provides a pharmaceutical composition which comprises an amount of either of the compounds having the structure:

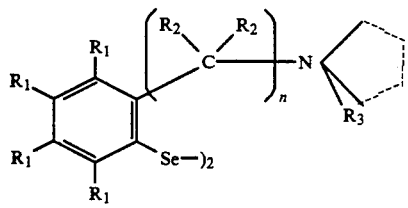

or having the structure:

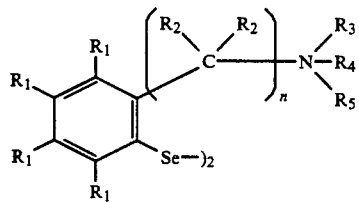

effective to reduce $H_2O_2$ and/or other peroxides in a subject afflicted with a peroxide-induced condition and a pharmaceutically acceptable carrier.

Further, the invention provides a pharmaceutical composition which comprises an amount of any of the compounds of the invention effective to reduce peroxide in a subject with a peroxide-induced condition and a pharmaceutically acceptable carrier. In addition, the pharmaceutical composition may include a cofactor, e.g. glutathione, ascorbic acid, cysteine, cystamine, dithiothreitol, or mercaptoethanol.

As used herein, the term "pharmaceutically acceptable carrier" encompasses any of the standard pharmaceutical carriers such as sterile solutions, tablets, coated tablets, and capsules. Typically such carriers contain excipients such as starch, milk, sugar, certain types of clay, gelatin, stearic acids or salts thereof, magensium or calcium sterate, talc, vegetable fats or oils, gums, glycols, or other known excipients. Such carriers may also include flavor and color additives or other ingredients. Compositions comprising such carriers are formulated by well known conventional methods.

The invention also provides a compound having the structure:

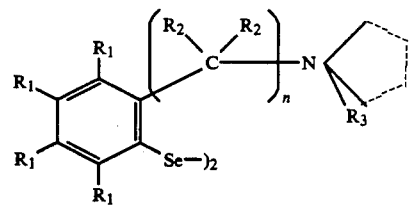

wherein n is an integer between 1 and 30; wherein each $R_1$ may be the same or different and represents an electron-donating group, an electron-withdrawing group, a lower alkyl group, a lower alkyl group containing one or more hydroxyl groups, or hydrogen; wherein each $R_2$ may be the same or different and represents a lower alkyl group, a lower alkyl group containing one or more hydroxyl groups, a hydroxyl group, an alcohol group, or hydrogen; wherein $R_3$ represents a hydrogen atom or a lower alkyl group which may be present or absent, which if present results in a positive charge on N; and wherein the dashed lines represent carbon-carbon bonds which may be present or absent, and wherein one or more $R_1$ are nitro groups, fluoro groups, fluoromethyl groups, or carboxyl groups.

The invention also provides a compound having the structure:

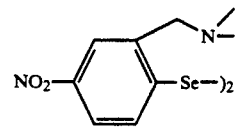

Additionally, the invention provides a compound having the structure:

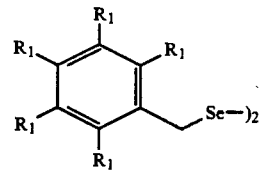

wherein each $R_1$ may be the same or different and represents an electron-donating group, an electron-withdrawing group, a lower alkyl group, a lower alkyl group containing one or more hydroxyl groups, or hydrogen.

The invention provides a compound having the structure:

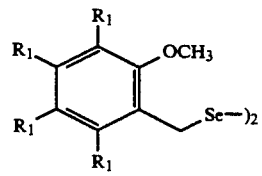

Further, the invention provides a compound having the structure:

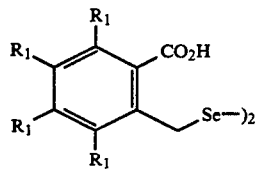

The invention provides a compound having the structure:

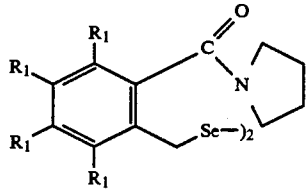

The invention also provides a compound having the structure:

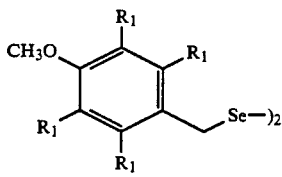

wherein X is hydrogen, a phenyl group, or a cyano group.

The invention further provides a compound having the structure:

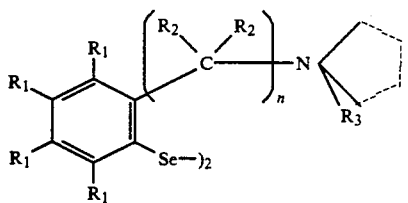

wherein n is an integer between 1 and 30; wherein each $R_1$ may be the same or different and represents an electron-donating group, an electron-withdrawing group, a lower alkyl group, a lower alkyl group containing one or more hydroxyl groups, or hydrogen; wherein each $R_2$ may be the same or different and represents a lower alkyl group, a lower alkyl group containing one or more hydroxyl groups, a hydroxyl group, an alcohol group, or hydrogen; wherein $R_3$ represents a hydrogen atom or a lower alkyl group which may be present or absent, which if present results in a positive charge on N; and wherein the dashed lines represent carbon-carbon bonds which may be present or absent, and wherein one or more $R_1$ are —$CH_2NC_4H_8$.

The invention provides a compound having the structure:

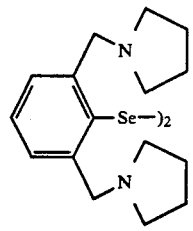

The invention also provides a compound having the structure:

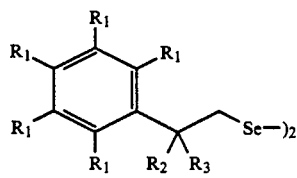

wherein each $R_1$ may be the same or different and represents an electron-donating group, an electron-withdrawing group, a lower alkyl group, or hydrogen; wherein $R_2$ is a hydrogen or lower alkyl group; and wherein $R_3$ is a hydrogen or lower alkyl group.

The invention also provides a compound described immediately above, wherein both $R_2$ and $R_3$ are methyl groups.

The invention also provides a compound having the following structure:

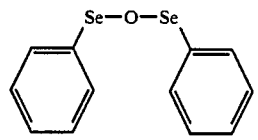

The invention also provides a composition comprising an amount of a compound having the following structure:

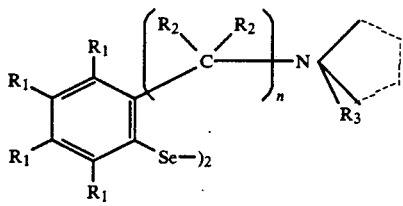

and an amount of a free radical trapper.

The invention also provides a method of treating a peroxide- or free radical-induced condition in a subject, e.g. a human being, which comprises administering, e.g. by topical, oral, intravenous, intraperitoneal, intramuscular, intradermal, or subcutaneous administration, to the subject an amount of a composition comprising (1) a compound having the structure:

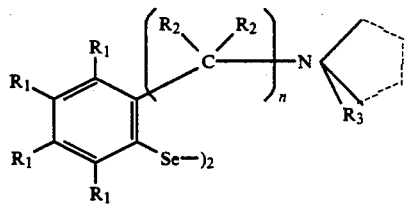

wherein n is an integer between 1 and 30; wherein each R₁ may be the same or different and represents an electron-donating group, an electron-withdrawing group, a lower alkyl group, a lower alkyl group containing one or more hydroxyl groups, or hydrogen; wherein each R₂ may be the same or different and represents a lower alkyl group, a lower alkyl group containing one or more hydroxyl groups, a hydroxyl group, an alcohol group, or hydrogen; wherein R₃ represents a hydrogen atom or a lower alkyl group which may be present or absent, which if present results in a positive charge on N; and wherein the dashed lines represent carbon-carbon bonds which may be present or absent, and (2) a free radical trapper, effective to reduce peroxide or free radicals in the subject and thereby treat the peroxide- or free radical-induced condition. Further, the peroxide- or free radical-induced condition may involve cataracts, inflammation of a tissue, eschemia, an allergic reaction, or pathology caused by oxidative stress. When the peroxide- or free radical-induced condition involves cataracts, administration is effected by, but is not limited to, topical contact to the surface of an eye.

The invention also provides a method of treating a peroxide- or free radical-induced condition in a subject which comprises administering to the subject an amount of a composition comprising (1) a compound of any of the compounds of the invention and (2) a free radical trapper, effective to reduce peroxide or free radicals in a subject and thereby treat the peroxide- or free radical-induced condition.

The invention also provides a compound having the structure:

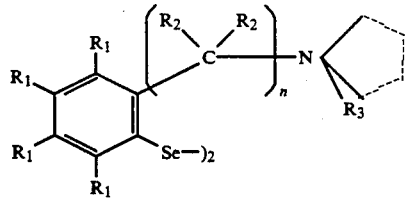

wherein n is an integer between 1 and 30; wherein each R₁ may be the same or different and represents an electron-donating group, an electron-withdrawing group, a lower alkyl group, a lower alkyl group containing one or more hydroxyl groups, hydrogen, or a free radical trapper; wherein each R₂ may be the same or different and represents a lower alkyl group, a lower alkyl group containing one or more hydroxyl groups, a hydroxyl group, an alcohol group, hydrogen, or a free radical trapper; wherein R₃ represents a hydrogen atom, a lower alkyl group, or a free radical trapper which may be present or absent, which if present results in a positive charge on N; and wherein the dashed lines represent carbon-carbon bonds which may be present or absent.

The invention further provides a compound as described immediately above, wherein the free radical trapper is 2,2,6,6-tetramethylpiperidine-1-oxyl. The invention also provides a compound as described immediately above wherein the free radical trapper is 2,2,5,5-tetramethyl-3-pyrroline-1-oxyl-3-carboxylic acid.

The invention further provides a compound having the structure:

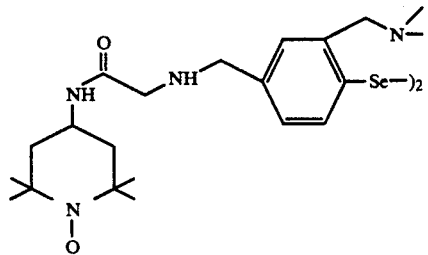

The invention further provides a compound having the structure:

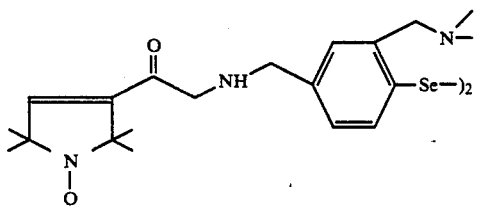

The invention also provides a method of treating a peroxide- or free radical-induced condition in a subject, e.g. a human being, which comprises administering, e.g. by topical, oral, intravenous, intraperitoneal, intramuscular, intradermal, or subcutaneous administration, to the subject an amount of a compound having the structure:

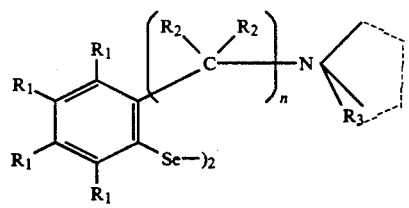

wherein n is an integer between 1 and 30; wherein each R₁ may be the same or different and represents an electron-donating group, an electron-withdrawing group, a lower alkyl group, a lower alkyl group containing one or more hydroxyl groups, hydrogen, or a free radical trapper; wherein each R₂ may be the same or different and represents a lower alkyl group, a lower alkyl group containing one or more hydroxyl groups, a hydroxyl group, an alcohol group, hydrogen, or a free radical trapper; wherein R₃ represents a hydrogen atom, a lower alkyl group, or a free radical trapper which may be present or absent, which if present results in a positive charge on N; and wherein the dashed lines represent carbon-carbon bonds which may be present or absent, effective to reduce peroxide or free radicals in the subject and thereby treat the peroxide- or free radical-induced condition. Further, the peroxide- or free radical-induced condition may involve cataracts, inflammation of a tissue, eschemia, an allergic reaction, or pathology caused by oxidative stress. Where the peroxide- or free radical-induced condition involves cataracts, admiistration is effected by, but is not limited to, topical contact to the surface of an eye.

This invention is illustrated in the Experimental Details section which follows. This section is set forth to aid in understanding the invention, but is not intented to, and should not be construed to, limit in any way the invention as set forth in the claims which follow.

EXPERIMENTAL DETAILS

Materials and Methods

All reactions were carried out under a nitrogen atmosphere. Melting points were determined in a Thomas capillary melting point apparatus and are uncorrected. PMR spectra were recorded on a General Electric QE-300 Spectrometer using the specified solvent. GC-MS analyses were obtained on a Hewlett-Parkard 5992B GC/MS system equipped with a capillary column. Exact masses were obtained from the NIH Rockefeller Mass Spectrometry Biotechnology Resource at Rockefeller University, New York, N.Y., by positive chemical ionization(CI). Gas chromatographic (GC) analyses were performed on a Varian Model 3700 gas chromatograph (flame ionization detector) using ⅛-in. columns packed with 2% OV-101–0.2% Carbowax on Chromasorb G. The standard temperature program is 60° C. (1 min) up to 300° C. at 20° C./min.

[2-[(N,-N-Dimethylamino)methyl]phenyl]lithium 17. n-Butyllithium (0.2 mol, 80 mL of a 2.5M solution in hexanes) was placed in a round-bottomed flask under nitrogen. N,N-dimethylbenzylamine (13.5g, 0.1 mol) and 215 mL of dry ether were added, and the resulting solution was allowed to stir at room temperature for 20 h. This was used as the stock solution of 17 and was approximately 0.34M in 17.

2,2 '-Diselenobis[[(N,N-dimethylamino)methyl]benzene] Bis(ydrochloride salt) 19. Under a nitrogen atmosphere, 2.0 g (25.3 mmol) of metallic selenium was added to 40 mL (13.6 mmol) of the stock solution of 17 and the mixture stirred at room temperature for 1 h. The resulting mixture (slightly green) was quenched by the addition of water and ether followed by bubbling air through it for 1 h. Layers were separated, and the aqueous phase was extracted with several portions of ether. The combined ethereal phases were washed with water and extracted with a 6M HCl solution. The combined extracts were concentrated in vacuo to give an oily residue, 18. This oil solidified upon trituration with ethanol-benzene to give bis(hydrochloride salt), 19, as an orange powder. Precipitation from ethanolbenzene provided 621 mg (21.4%) of yellow powder (darkening at 219° C., mp 224°–225° C. dec): GC retention time (free base)=8.56 min; TLC (free base, silica gel, 20% ethyl acetateligroin) $R_f$=0.35; $^1$H NMR (300 MHz, D$_2$O) δ7.73 (d, 1 H, 4.2 Hz), 7.45 (m, 2 H), 7.36 (m, 1 H), 3.98 (s, 2 H), 2.67 (s, 6 H); HRMS (from free base/Cl) (C$_{18}$ H$_{25}$N$_2$ Se$_2$)H+ 429.0222 [calculated for (C$_{18}$H$_{25}$N$_2$Se$_2$)H+ 429.0348].

1-Bromo-2-(pyrrolidin-1-ylmethyl benzene 22. 2-Bromobenzyl bromide 21 (3.0 g, 12 mmol) was dissolved in 5 mL of methylene chloride, and 2 equiv (22.4 mmol, 2.2 mL) of pyrrolidine 20 was added dropwise. The initial reaction was exothermic. After the addition was complete, the mixture was allowed to stir at room temperature overnight; it was then poured into water and ether, the layers were separated, and the ether layer was washed with water, dried (KOH), and concentrated to a yellow oil. Distillation provided 2.346 g (81%) of the amine 22, boiling at 104°–107° C.(20 mmHg): GC retention time=3.92 min; TLC (silica gel, 20% ethyl acetate-ligroin) $R_f$=0.39; IR (neat) 2950, 2780, 1600, 1450, 1430, 1025, 750; 1 H NMR (300 MHz, CDCl$_3$) δ7.54 (m, 2 H) , 7.28 (m, 1 H) , 7.09 (m, 1 H), 3.74 (s, 2 H), 2.60 (m, 4 H), 1.81 (m, 4 H); GC-MS(%abundance) 241 (70), 240 (100), 239 (71), 238 (93), 171 (43), 169 (45), 84 (57), 70 (20), 42 (43).

2,2'-Diselenobis[(pyrrolidin-1-ylinethyl)benzene]Bis (hydrochloride salt) 25. The bromide 22 (480 mg, 2 mmol) was dissolved in 4 mL of dry THF and the resulting solution cooled to −78° C. n-Butyllithiuin (2.0 mL of a 2M solution in hexanes, 2 equiv) was added dropwise via syringe. After the addition was complete, the mixture was stirred at −78° C. for 1 h. Selenium (2 equiv, 4 mmol, 316 mg) was added followed by anhydrous MgBr$_2$ (4 mmol). This mixture was allowed to stir overnight. Selenium (2 portions of 35 mg each) was added, and the mixture turned dark red. The mixture was then poured into water and ether, the ether layer was separated, and the aqueous phase was extracted with ether. The combined ethereal extracts were dried (Na$_2$SO$_4$) and concentrated to give an oily residue. The residue was taken up in 6M HCl solution and the solution washed with methylene chloride several times. The aqueous solution was then concentrated in vacuo to give a resinous residue (432 mg). This material was dissolved in the minimum amount of ethanol, benzene was added, and the compound was allowed to precipitate. This procedure provided 250 mg (45%) of 25 as a yellow powder (darkening at 216° C., mp 229°–230° C. dec): GC retention time (free base)=10.12 min; TLC (free base, silica gel, 20% ethyl acetate-ligroin) $R_f$=0.21; $^1$H NMR (300 MHz, D$_2$O) δ7.73 (d, 1 H, 4.2 Hz), 7.45 (m, 2 H), 7.36 (m, 1 H), 4.09 (s, 2 H), 3.30 (m, 2 H), 2.95 (m, 2 H), 1.99 (m, 2 H), 1.83 (m, 2 H); HRMS (from free base/Cl) (C$_{22}$H$_{28}$SN$_2$Se$_2$)H+ 481.0661 [calculated for (C$_{22}$H$_{28}$N$_2$ Se$_2$)H+ 481.0654].

[[2-[{N$_3$N-Dimethylamino)methyl]phenyl]seleno]-benzene 26. The aryllithium, 17 (20 mL 6.6 mmol) solution was placed in a flask under nitrogen. Diphenyl diselenide (2.375 g, 7.6 mmol) in 20 mL of dry ether was added dropwise over the course of 5 min. The resulting solution was allowed to stir at room temperature for 1 h. The solution was diluted with ether, washed well with water, dried (Na$_2$SO$_4$), and concentrated. The yellow residual oil was distilled (kugelrohr, 0.5 Torr) at 145°–155° C. (yield 1.302 g, 68%). Material obtained in this way contained a small amount of diphenyl diselenide. This impurity could be removed by purification by preparative TLC on silica gel eluting with 20% ethyl acetate-ligroin containing 1% triethylamine ($R_f$=0.38). In this way 145 mg of distilled material gave 101 mg of purified 26 as a tan, mobile oil. Upon standing at room temperature, the oil solidified to a waxy, tan solid (mp 48° C.): GC retention time=5.88 min; $^1$H NMR (300 MHz, CDCl$_3$) δ7.56-7.0 (m, 9 H), 3.52(s, 2 H), 2.24 (s, 6 H); GC—MS (% abundance) 291 (82), 276, (30), 165 (52), 132 (59), 121 (100), 91 (32), 58 (57).

[[2-(Pyrrolidin-1-ylmethyl)phenyl]seleno]benzene 27. The bromide 22 (240 mg, 1 mmol) was dissolved in 3 mL of dry THF and the resulting solution cooled to −78° C. under nitrogen. n-Butyllithium (2 equiv, 2 mmol, 1 ml of a 2.0M solution in hexanes) was added dropwise via syringe and the mixture stirred for an additional hour at −78° C. after the addition was complete. Diphenyl diselenide (1 equiv, 1 mmol, 212 mg) in 5 mL of THF was added dropwise and the mixture stirred overnight. A few drops of saturated ammonium chloride solution were added, salts were filtered, and the solution was concentrated to give the crude 27. Purification by preparative TLC on silica gel, eluting with 20% ethyl acetate-ligroin containing 1% triethylamine ( $R_f$=0.42), gave pure 27 (104 mg, 33%): GC retention time=7.12 min; $^1$H NMR (300 MHz, CDCl$_3$) δ7.56–7.0 (m, 9 H), 3.75 (s, 2 H), 2.52 (m, 4 H), 1.77 (m, 4 H).

Synthesis of Amines

Diphenyl diselenide, 16 was obtained from Aldrich and used without further purification.

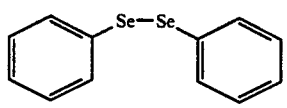

16

Diaminodiselenide 18 was synthesized in two steps from commercially available materials (eq 1). Orthometalation of N,N-dimethylbenzylamine was readily accomplished according to procedure of Klein and Hauser (7). Thus, N,N-dimethylbenzylamine was treated with a slight excess of n-butyllithium in ether-hexane at room temperature for 24 h and the resulting solution of aryllithium 17 treated with metallic selenium. The resulting arylselenol was oxidized with air to the corresponding diselenide (8). The oily product was most easily handled as its bis(hydrochloride salt) 19.

The amine 22 required for the synthesis of 24 was readily prepared by alkylation of pyrrolidone 20 with 2-bromobenzyl bromide 21. The corresponding Grignard reagent failed to form upon treatment of 22 with magnesium. Halogen-metal exchange with 2 equiv of n-butyllithium at −78° C. in THF proceeded smoothly to give the desired aryllithium 23. This reagent readily reacted with metallic selenium in the presence of anhydrous MgCl$_2$ to give the desired diselenide 24. As in the case of 18, the diselenide was converted for

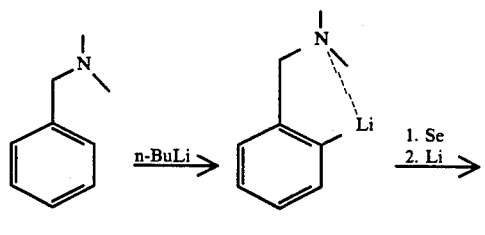

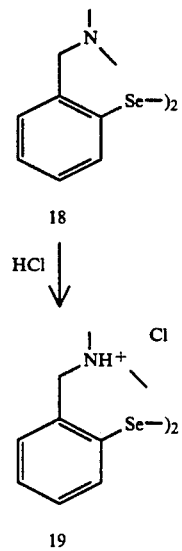

ease of handling into the bis(hydrochloride salt) 25.

The synthesis of the diaryl selenide, 26 was accomplished in a straightforward manner by the reaction of aryllithium, 17 with diphenyl diselenide. Diaryl selenide 26 proved to be much easier to handle than the corresponding diselenides and could thus be purified by chromatography.

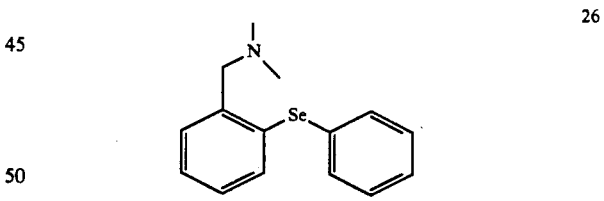

The synthesis of the diaryl selenide, 27 was achieved by the reaction of aryllithium, 23, with diphenyl diselenide.

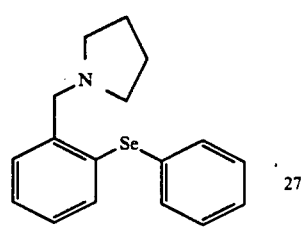

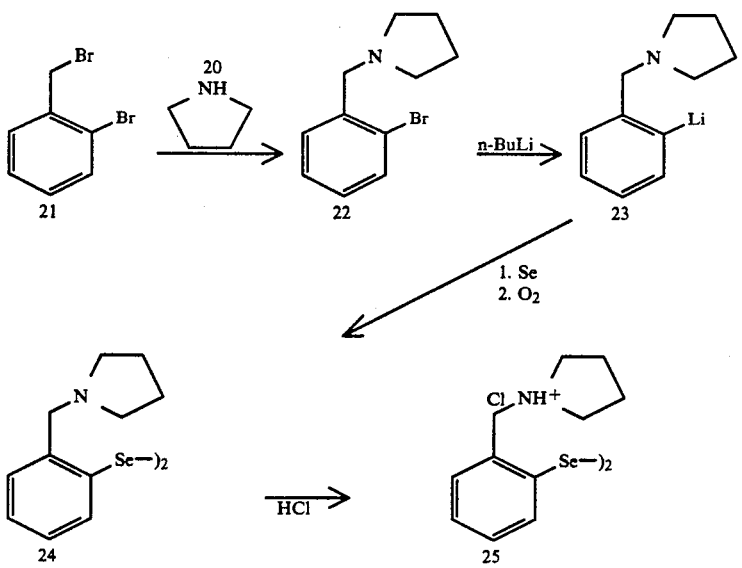

RESULTS AND DISCUSSION

Glutathione peroxidase activity of the compounds was determined with a modification of the method of Wendel (9) using hydrogen peroxide as the substrate in the presence of GSH. Glutathione reductase was used to reduce the oxidized GSH with NADPH as a cofactor (eq 2). The decrease in NADPH monitored spectrophotometrically at 366 nm is a measure of GSH peroxidase activity (see eq 2–4). The assay mixture $$2GSH + H_2O_2 \xrightarrow{GSH\ PEROXIDASE} GSSG + 2H_2O \quad (eq\ 2)$$

$$GSSG + NADPH + H^+ \xrightarrow{GSH\ reductase} 2GSH + NADP^+ \quad (eq\ 3)$$

$$H^+ + NADPH + H_2O_2 \longrightarrow NADP^+ + 2H_2O \quad (eq\ 4)$$

(700 μL) contains 50 mM potassium phosphate buffer, pH 7.0, 1 mM EDTA, 1 mM sodium azide, 1 mM GSH, 0.25 mM NADPH, 1 unit of GSSG reductase, and an appropriate amount of test compound (usually 2–20 μM final concentration). The absorbance at 366 nm was recorded for a few minutes to estimate the background and stability of the preparation. Reaction was initiated by the subsequent addition of hydrogen peroxide to 500 μM. Appropriate blanks were run in the absence of test compound and in some cases with test compound and $H_2O_2$ in the absence of NADPH. The results are shown in Table I. The relative activities of the compounds prepared in this study were compared to that of GSH peroxidase. Values for Ebselen 3 and compound 2 and are included.

For most compounds, the initial rate of NADPH utilization was determined at six concentrations ranging over more than a 10-fold difference in concentration. The rates in all cases were found to be a linear function of concentration, suggesting that the compounds were saturated with substrate. Under such conditions, the initial rates can be assumed to be maximum rates and $V_{max}=kE_t$, where V=maximum velocity of the reaction and $E_T$ represents the total concentration of the GSH peroxidase analogue. The K value represents the turnover number, i.e., the number of $H_2O_2$ molecules degraded per minute per molecule of analog. These values are shown in Table I. It was found that the reaction rates remain linear for at least 5 min. Thus, for example, for 25, 55.5 molecules of $H_2O_2$ are degraded per molecule of compound in five minutes without any loss of catalytic activity. No indication of loss of catalytic activity was observed. While these turnover numbers are very low compared to that of GSH peroxidase, they are in the same range as have been reported for enzymes such as lysozyme (30 μmole per minute per μmole).

Several conclusions can be drawn from these results. The observation that diphenyl diselenide 16 exhibits approximately twice the activity of Ebselen's 3rules out the assumption that a selenium-nitrogen bond is necessary for glutathione peroxidase activity. This conclusion was tentatively suggested by the activity found in 2. It is also consistent with the

TABLE I

| Compound | Activity[a] | rel GSH Peroxidase Activity[b] |
|---|---|---|
| 2 | 0.034 | 0.03 |
| 3 | 0.99 | 0.88 |
| 16 | 1.95 | 1.7 |
| 26 | 0.050 | 0.043 |
| 27 | 0.046 | 0.04 |
| 19 | 10.5 | 9.1 |
| 25 | 11.1 | 9.7 |

[a]Micromoles of NADPH utilized per minute per micromole.
[b]Based upon GSH peroxidase activity equal to 10,000.

Figure 1:
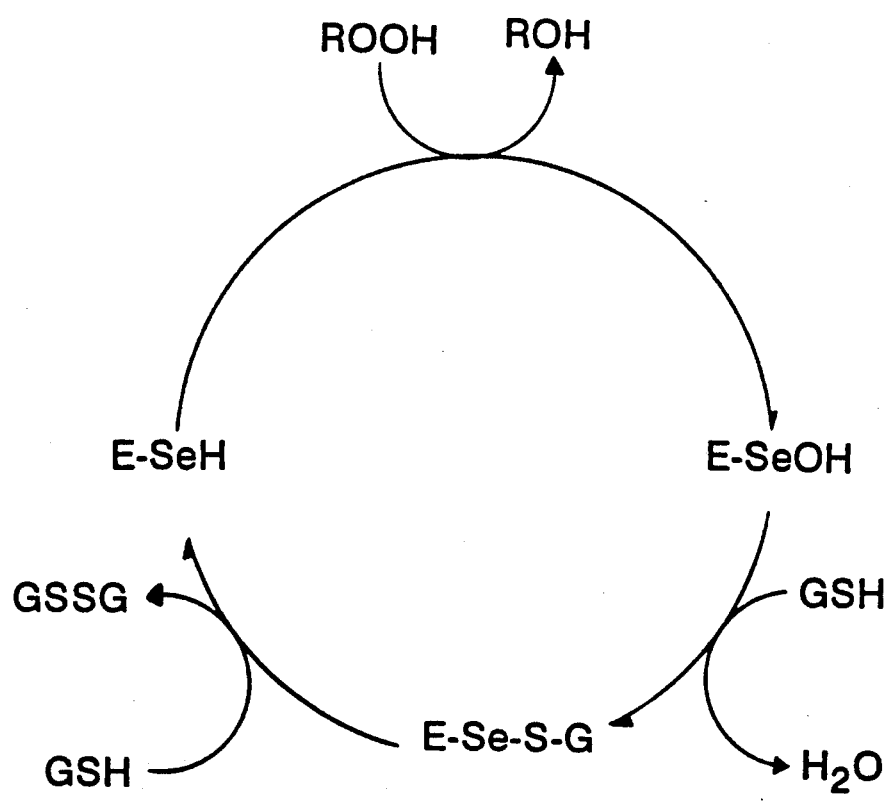
FIG. 1 illustrates the two-step reduction of seleninic acid utilizing 2 mol of GSH/mol of enzyme.
Figure 2:
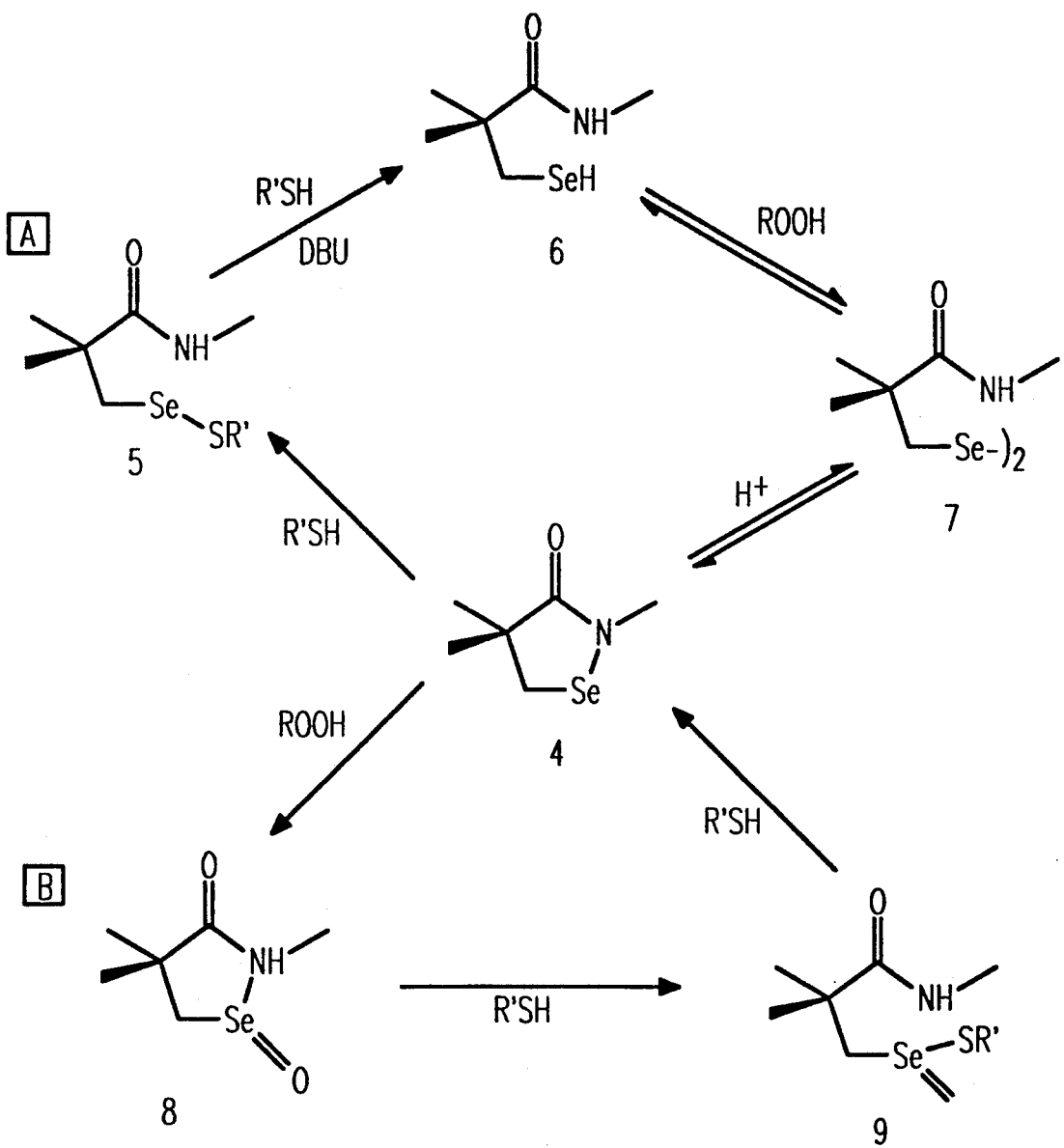
FIG. 2 is a diagram of the oxidation-reduction chemistry of 4.
Figure 3:
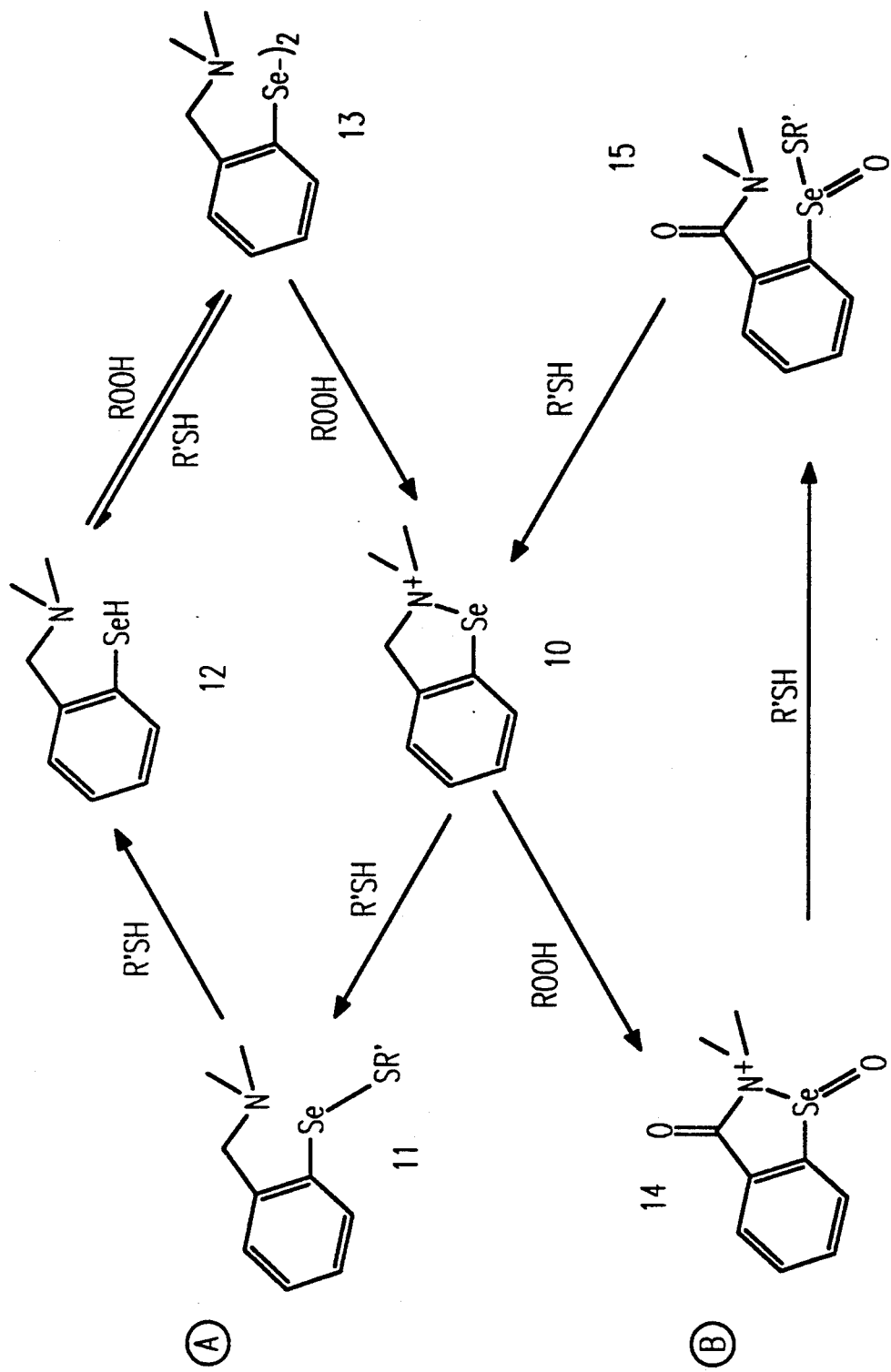
FIG. 3 illustrates the chemical process for producing tertiary amines with glutathione peroxidase activity.

Several conclusions can be drawn from these results. The observation that diphenyl diselenide 16 exhibits approximately twice the activity of Ebselen's rules out the assumption that a selenium-nitrogen bond is necessary for glutathione peroxidase activity. This conclusion was tentatively suggested by the activity found in 2. It is also consistent with the observations of Reich and Jasperse (6) since one could reasonably propose that the catalytic cycle A (FIG. 2) completely by passes the selenamide, 4 with nucleophilic attack of thiolate occurring on the diselenide 7. Support of this view is found in the observation that oxidation of 6 led to the formation of 7 and not 4(6).

Also clear from the results in the table is the requirement that the disubstituted selenium atom must have at least one selenium-heteroatom bond. The diaryl selenides 26 and 27 show small amounts of activity. This activity may be due to trace amounts of diphenyl diselenide present in the compounds as impurities remaining from their syntheses.

The tertiary amine analogue of 16, 19, and 25 are approximately 5.5-fold more active than 16. The role of the tertiary amine in the catalysis of the reaction may be that which was suggested earlier. The amine may serve to deprotonate the thiol sulfhydryl group and thus provide a high local concentration of nucleophilic thiolate anion. Another possible mode of catalysis might be that the conjugate acid of the amine, the ammonium ion, obtained upon abstraction of a proton from a sulfhydryl group serves as a proton source, facilitating the reduction of hydrogen peroxide to water.

The most active compounds, 19 and 25, are approximately 10.5 times more active than Ebelson 3 and indicate that it is possible to produce relatively simple compounds that have significant GSH peroxidase activity.

In summary, we prepared organoselenium compounds which show catalytic activity in the enzyme assay for the selenoenzyme glutathione peroxidase. These compounds were designed on the basis of the known chemistry of models for the active site of glutathione peroxidase. Diphenyl diselenide 16 has been shown to be approximately 2-fold more active in this assay then the most active compound previously known. Introduction of tertiary amine substituents onto the aromatic nucleus at a position ortho to the selenium atom in 19 and 25 results in a further approximately 5-fold increase in activity. Diaryl selenides 26 and 27 are demonstrated to show no significant glutathione peroxidase activity.

bility of the lens. After 10 minutes in the presence of 100 μM peroxide, there is an approximately fifty percent drop in activity. With 200 μM peroxide, the activity decreases six-fold. In the presence of the purified mimic, the glyceraldehyde-3-phosphate dehydrogenase acivity is protected.

Figure 5:
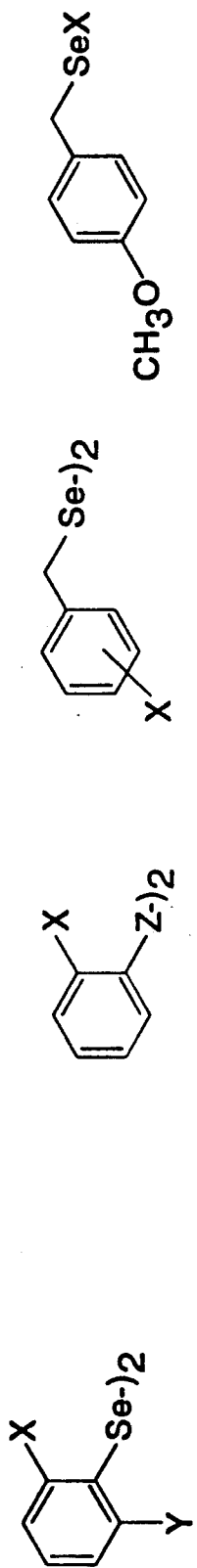
FIG. 5 presents the glutathione peroxide activity of a variety of compounds that have been synthesized.
Figure 5:
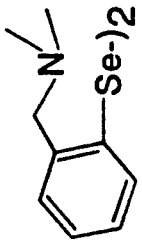

FIG. 5 presents the glutathione peroxide activity of a variety of compounds that have been synthesized. As can be seen from the figure, the selenium atom can be one carbon away from the aromatic ring and still exert glutathione peroxide activity.

Figure 6:
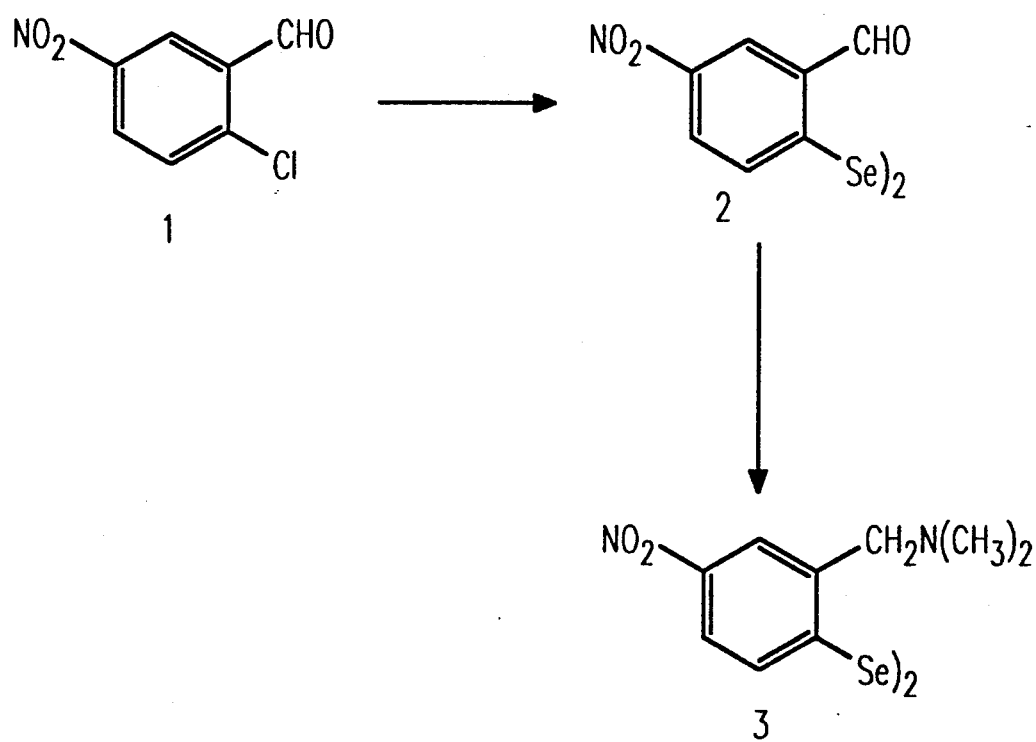

FIG. 6 presents the synthesis of the following compound:

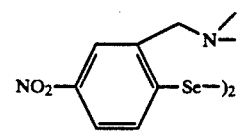

The synthesis was carried out as described by Buu-Hoi, Bull. Soc. Chim. Belges., Vol. 79, p. 601 (1970). The commercially available compound 1 was reacted with $Na_2Se_2$ to give compound 2. Compound 2 may be converted to compound 3 by reductive amination using dimethyl amine and sodium cyanoborohydride.

TABLE 3

Approximate Distribution of Selenides in GSH Px Mimics*

| | Selenides | | |
|---|---|---|---|
| | Di | Tri | Tetra |
| Unreduced | 88 | 11 | 1 |
| DTT | 92 | 8 | 0 |
| Na—BH₄ | 95 | 5 | 0 |
| Alternate Synthesis | 100 | 0 | 0 |

*determined by mass spectrophotometric peak intensities.

Table 3 shows the purification of the mimic,

EXPERIMENTAL DETAILS—PART 2

TABLE 2

| | Glyceraldehyde-3-Phosphate Dehydrogenase Activity* | | | | | | | | |
|---|---|---|---|---|---|---|---|---|---|
| | | | | H₂O₂ | | | | | |
| | — | | | 100 μM | | | 200 μM | | |
| Minutes | Control | Purified Mimic (10 μM) | Ebselen (100 μM) | Control | Purified Mimic (10 μM) | Ebselen (100 μM) | Control | Purified Mimic (10 μM) | Ebselen (100 μM) |
| 0 | — | — | — | — | — | — | 29 ± 2.1 | 26 ± 0.7 | 28 ± 0.9 |
| 5 | — | — | — | 16 ± 0.2 | 27 ± 1.2 | 21 ± 0.3 | 7.4 ± 1.1 | 26 ± 0.5 | 15 ± 0.1 |
| 10 | 32 ± 0.9 | 28 ± 1.7 | 27 ± 1.4 | 13 ± 0.2 | 27 ± 0.7 | 17 ± 0.1 | 5.1 ± 0.3 | 27 ± 1.0 | 7.6 ± 0.7 |

*Activity per 100,000 cells in munits ± S.D. 1 munits = utilization of 1 nmole of NAD/ml/minute Table 2 shows that the compound having the structure:

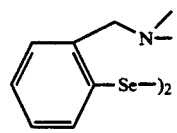

(called "purified mimic" in Table 2) protects lens epithelial cells from peroxide stress using concentrations of peroxide that would cause cataract. Table 2 shows the extent to which the purified mimic is able to protect lens epithelial cell glyceraldehyde-3-phosphate dehydrogenase activity from peroxide stress. Glyceraldehyde-3-phosphate dehydrogenase activity is critical to the via-

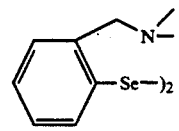

, in which extraneous selenium has been eliminated from the compound. The purified compounds have less cell toxicity. The mimic was purified by reduction with dithiothreitol or NaBH₄. Also, the mimic was prepared by an alternate synthetic route that does not utilize selenium.

To purify by reduction with dithiothreitol, the selenides were placed in a solution with a seven-fold excess of dithiothreitol. After waiting five minutes, a second addition of a seven-fold excess of dithiothreitol was added. After 1 minute, the mixture was acidified with trifluoroacetic acid to a final 1 concentration of trifluoroacetic acid. The selenides were isolated by HPLC using trifluoroacetic acid at one tenth percent using a linear gradient of 0-80 percent acetonitrile. To purify by reduction with NaBH$_4$, the selenides were contacted with NaBH$_4$ in methanol for one hour at room temperature.

The alternate synthetic route to the mimic is illustrated in FIG. 7. Commercially available ethyl-2-amino benzoate (Aldrich) was treated with excess lithium dimethylamide prepared in situ by adding two equivalents of n-butyl lithium to dimethyl amine hydrochloride. The resulting amide 2 was then diazotonized by dissolving it in 6N HCl, cooling to 0° C., and adding an aqueous solution of sodium nitrite (1.2 equivalents). After 45 minutes the excess sodium nitrite was destroyed by adding urea, and the pH was adjusted to 6 by adding sodium acetate.

Aqueous potassium selenocyanate was then added slowly. After 24 hours at room temperature the reaction mixture was worked up. The resulting amide-selenocyanate 3 was then reacted with lithium aluminum hydroxide in refluxing tetrahydrofuran for two and a half hours. The reaction mixture was then exposed to air overnight and worked up to give diselenide 4 with all analytical data (1HNMR, 13 CNMR, mass spectrometry, melting point) matching that of the known compound.

TABLE 4

| Substrate Dependence | | |
|---|---|---|
| | H$_2$O$_2$ Utilized nmoles/ml/3 min/15 µM | |
| Substrate 1.5 mM | spectro- photometric | electro- chemical |
| Ascorbic Acid | — | 80 |
| Cysteine | 323 | 298 |
| Cystamine | 320 | 314 |
| Dithiothreitol | 358 | 341 |
| Glutathione | 294 | 305 |
| Mercaptoethanol | 245 | — |

Table 4 shows the substrate dependence of the dimethyl amino diselenide,

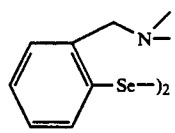

, reduced and purified by HPLC. The ability of the dimethyl amino diselenides to degrade H$_2$O$_2$ was followed either electrochemically with a YSI meter or spectrophotometrically utilizing ferrithiocyanate color formation on oxidation of ferrous ammonium sulfate in the presence of potassium thiocyanate. It should be noted that the mimic can utilize the reducing potential of thiol and nonthiol components.

The H$_2$O$_2$ spectrophotometric assay is conducted with 500 µM H$_2$O$_2$, 15 µM mimic (dimethylaminodiselenide) and a cofactor (GSH, DTT, etc.), 1.5 mM, and a phosphate buffer, pH 7.0, 25 mM. 100 µl samples are taken for determination of H$_2$O$_2$ as a function of time. The peroxide assay is conducted as follows. 100 µl samples are added to a test tube containing 900 µl H$_2$O, 50 µl of 50% TCA (final TCA concentration is 5%). 50 µl of 30 mM ferrous ammonium sulfate, and 50 µl of 2.5M KSCN (potassium thiocyanate) are then added. Ten minutes later, the solution is analyzed and H$_2$O concentration determined based on standards treated in a similar manner.

FIG. 8 shows the absorbtion spectrum of the mimic,

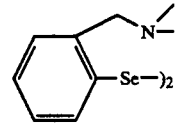

Figure 4:
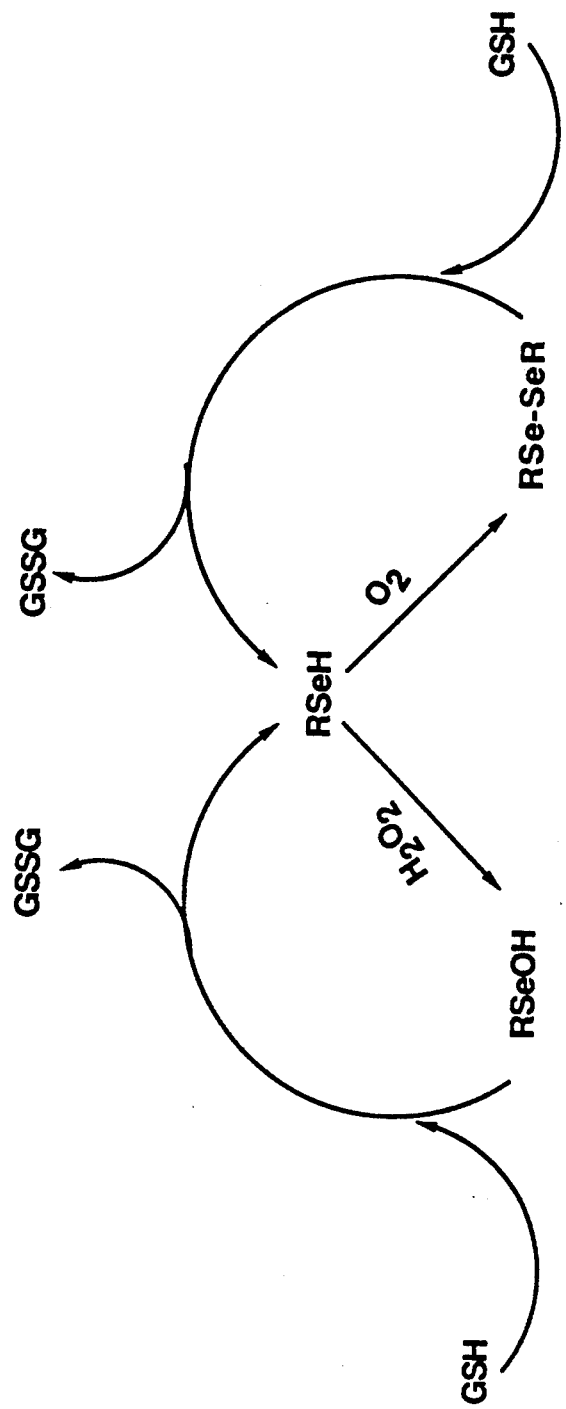
FIG. 4 illustrates the competition between hydrogen peroxide and oxygen for selenol (RSeH).
Figure 8A:
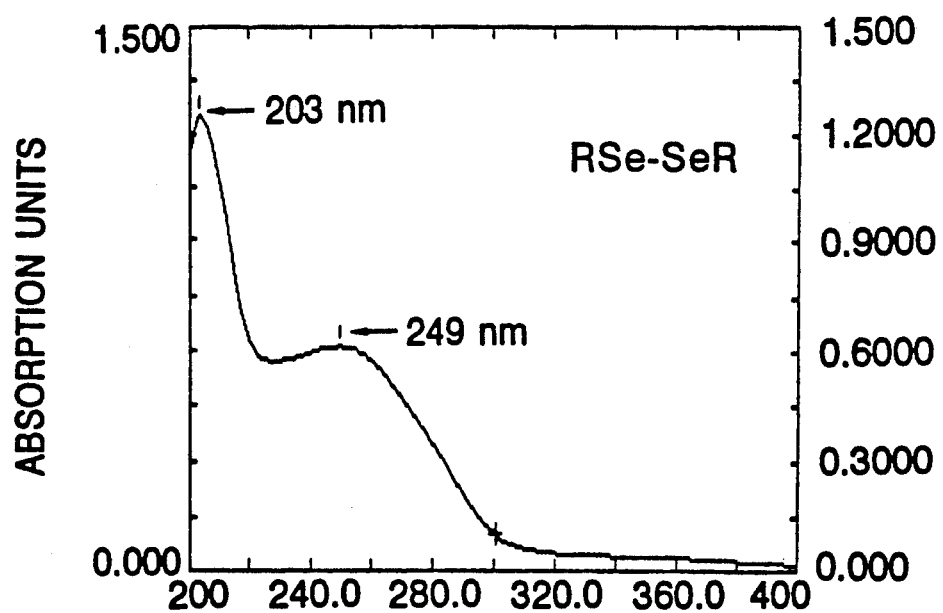
Figure 8B:
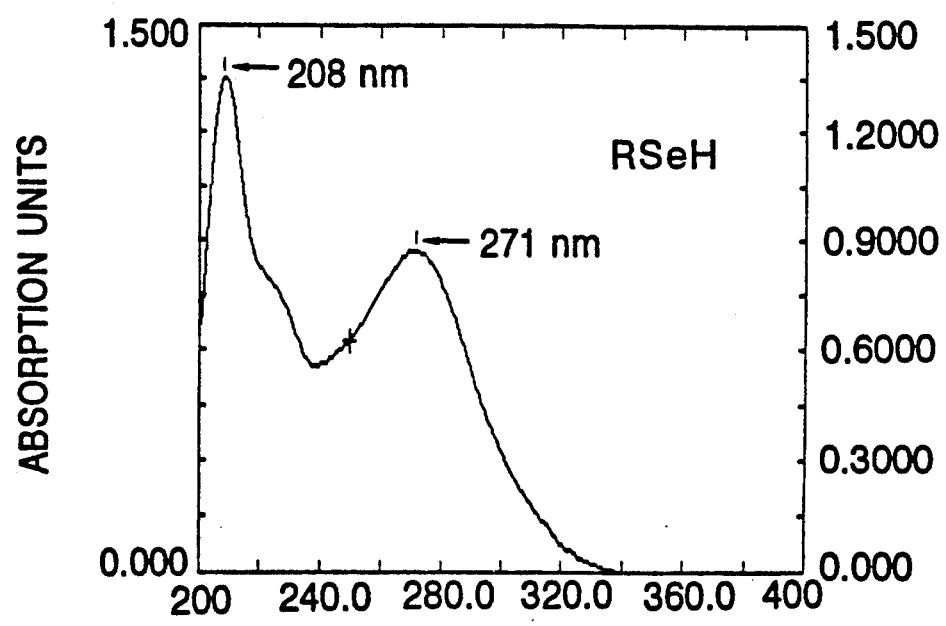
Figure 8C:
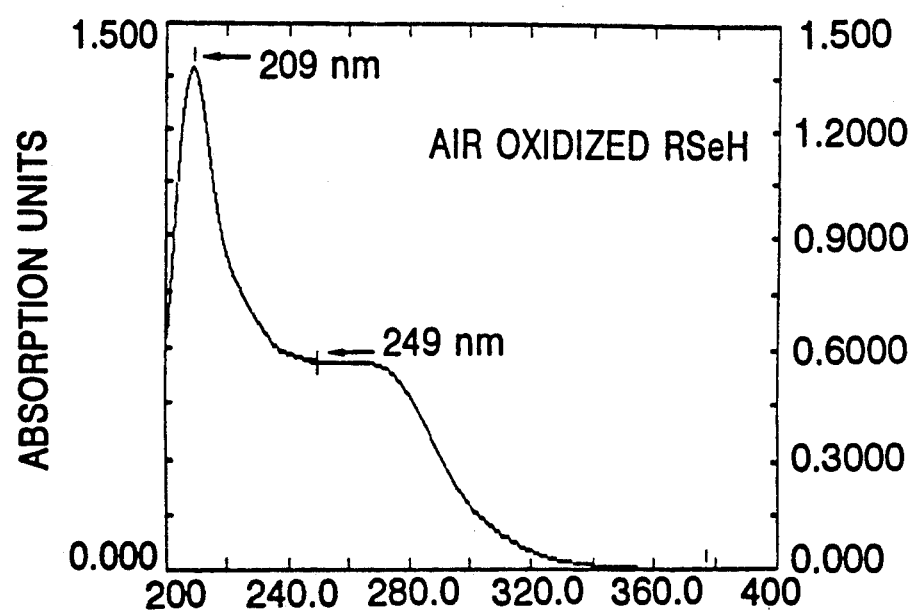
Figure 8D:
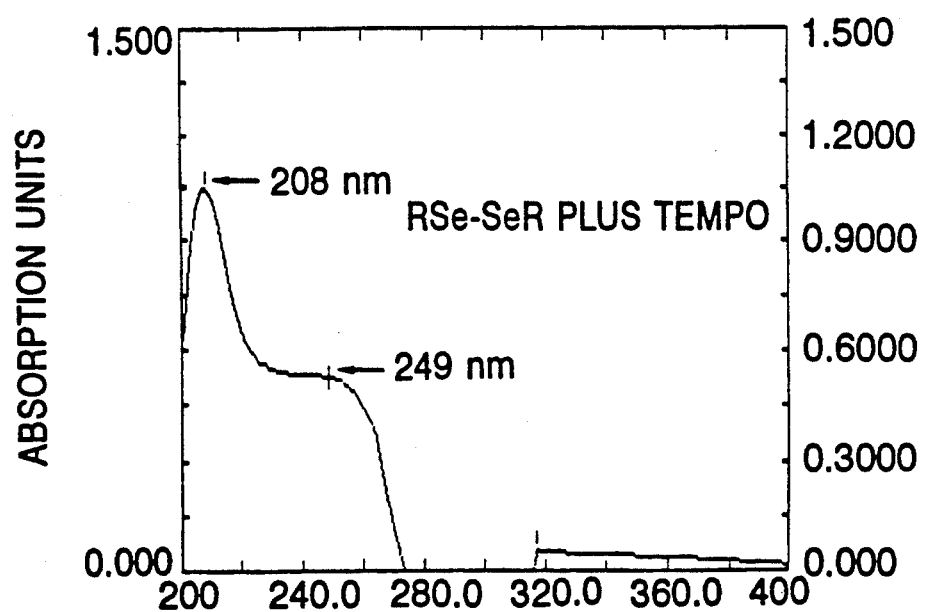
Figure 8E:
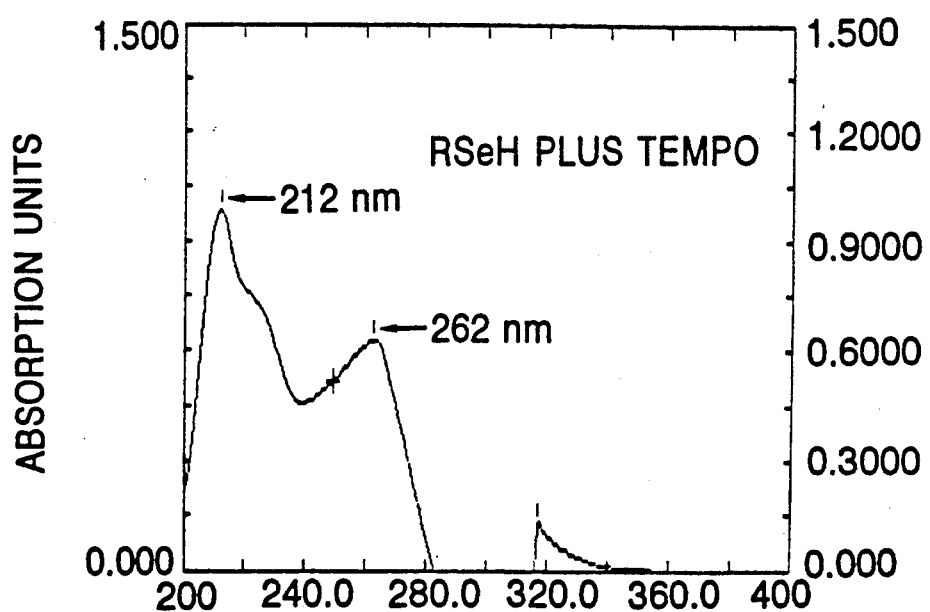
Figure 8F:
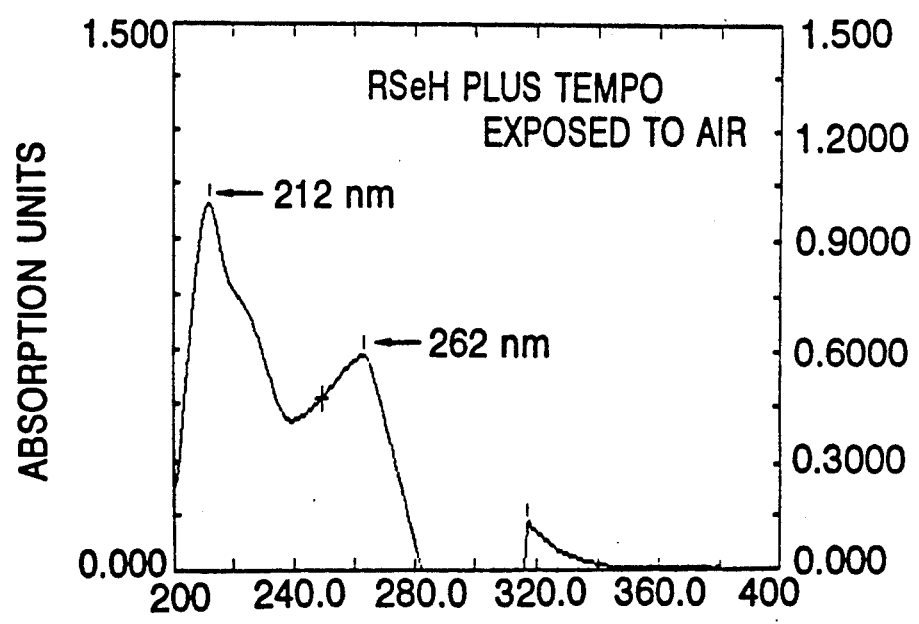

, in the oxidized form (8(a)), reduced by GSH (8(b)), and oxidized by air (8(c)). As can be seen from the figures, the mimic oxidized by air (8(c)) shows the spectrum of RSe-SeR (8(a)). This indicates that the air oxidation of the mimic (see FIG. 4) results in the production of RSe-SeR. FIG. 8(d), 8(e), and 8(f) show the mimic and 2,2,6,6-tetramethylpiperidine-1-oxyl (Tempo), with mimic in the oxidized form (8(d)), reduced by GSH (8(e)), and after exposure to air (8(f)). As can be seen from the figures, the presence of Tempo prevents the formation of RSe-RSe. RSeH plus Tempo exposed to air has the same spectrum as RSeH plus Tempo. These results indicate that the oxidation of RSeH by oxygen can be blocked by the addition of a free radical trapper. This result is important because blocking the oxidation by oxygen prevents wasteful utilization of reducing components (cofactors) which will keep the selenide in the reduced selenol form (see FIG. 4).

The absorption spectra in FIG. 8 were obtained as follows. Purified mimic, 50 µM, was reduced at pH 7.0, 25mM phosphate buffer with glutathione, 110 µM. Reduced spectra was obtained after five minutes by utilizing oxidized glutathione, 50 µM as a background. Air was then bubbled through the solution for 10 to 15 minutes and the spectra were taken again. When Tempo was used, it was at a concentration of 1 mM and was also added to the background.

FIG. 9 shows that lens epithelial cells exposed to H$_2$O$_2$, 50-75 µM, for three minutes sustain considerable DNA damage. The presence of the purified dimethyl amino diselenide,

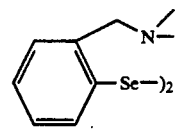

, 20-40 µM, reduces the damage considerably. However, the dimethyl amino diselenide itself causes some damage. The damage is reduced by the addition of Tempo, 1.0 mM. Furthermore, we have previously shown that the DNA damage caused by generation of the hydroxyl radical arising from H$_2$O$_2$ by the Fenton reaction. It would appear that dimethyl amino diselenide is also capable of generating free radicals which cause DNA damage. The presence of the free radical trapper essentially eliminates the damage.

The DNA damage in FIG. 9 was determined by the method of alkaline elution, described below.

Method of Alkaline Elution

1. Cell Preparation and DNA Labeling

Actively growing cells were obtained from second passage monolayer cultures derived from primary explants of young bovine lens epithelial cells. These cultures were prepared from young calf lenses and maintained as described previously (Spector, et al., *J. Biol. Chem.*, Vol. 263, pp. 4984–4990 (1988) and Spector, et al., *Curr. Eye Res.*, Vol. 4, pp. 1289–12951(1985).

Uniformly labeled DNA was obtained as follows: $5.0 \times 10^4$ cells were plated in 35-mm culture dishes (Corning) in 2 ml of Eagle's minimum essential medium (Gibco Laboratories, cat. No. 410-1500) containing 10% fetal bovine serum (Hy-Clone Laboratories), 100 U/ml penicillin, 100 μg/ml streptomycin, and 0.25 μg/ml amphotericin B. The cells were incubated with 0.2 μCi/ml [$^3$H]thymidine (50 Ci/mmole, ICN Radiochemicals) and 1μM unlabeled thymidine for 7 days. After removal of the radioactive medium, the monolayers were washed twice with unlabeled medium containing 10 μM thymidine and then incubated for 2 days with i additional change of medium.

2. $H_2O_2$ Exposure

Monolayers were washed once with Eagle's minimum essential medium prewarmed to 37° C. (without serum) and then incubated in this medium for 30 min before the start of each experiment. Prewarmed medium containing the indicated concentrations of $H_2O_2$ was added for 3 min at which time the medium was quickly removed and 2 ml of fresh medium containing 2.0 μg/ml catalase (Sigma Chemical Co.) was added for an additional 3 min. Occasionally, peroxide measurements were made using a YSI model 27 meter utilizing a blank membrane (Yellow Spring Instrument Co., Yellow Spring, Ohio). The monolayers were then quickly rinsed twice with 1 ml of ice-cold Dulbecco's phosphate-buffered saline under reduced lighting and the plates scraped with a rubber policeman in 0.75 ml of this solution. The cell suspension was then passed 4 times through an 18-gauge needle to disperse the cells (confirmed by microscopic observation). This procedure was repeated with an additional 0.75 ml of solution. The resulting 1.5 ml cell suspension was used immediately.

3. Elution Assays

Alkaline elution was performed as described (Kohn et al., 1976) using 25-mm polycarbonate filters with 2.0-μm pores (Nucleopore Corp.), 0.5 mg/ml proteinass K was utilized and DNA was eluted in the dark at 2.5 ml/h with 18 ml of 25 mM Na$_2$EDTA and 0.1% SDS (Schwartz-Mann Ultrapure) buffered to pH 12.15 with tetrapropylammonium hydroxide. Fractions were collected every hour and radioactivity was determined by scintillation counting with 16 ml of Ecolite (ICN Radiochemicals) containing 0.88% glacial acetic acid. Strand scission factors were calculated as described (Cantoni et al., *Biochim. Biophys. Acta.*, Vol. 867, pp. 135–143 (1986)).

The free radical trapper can either be mixed with the diselenide, as seen in FIG. 9, or attached directly to the selenol. The attachment of Tempo and Tempo-derivatives to numerous types of compounds is well known (*Biochemistry*, Vol. 24, p. 6591 (1982), *Biochemistry*, Vol. 26, p. 5534 (1987)). FIG. 10 illustrates two methods of attaching a free radical trapper to a diselenide. Commercially available free radical trapper 2 can be reacted with compound 1 to produce compound 3. Also, commercially available free radical trapper 4 can be reacted with compound 1 to produce compound 5.

REFERENCES

1. Chance, B. Boveris, A., Nakase, Y., Sies, H. (1978) Functions of Glutathione in Liver and Kidney (Springer Verlag, Berlin,), pp 95–106.
2. Epp, O., Ladenstein, R., Wendel, A. (1983) Eur. J. Biochem. 133:51–69.
3. Spector, A. (1984) Invest. Ophthal. Vis. Sci. 1984, 25:130–146.
4. Unpublished Observations.
5. Wendel, A. (1985) European Patent, 165:534.
6. Reich, N. J., Jasperse, C. P. (1987) J. Am. Chem. Soc., 109:5549–5551.
7. Klein, K. P., Hauser, C. R. J. (1967) Org. Chem., 32:1479–1483.
8. Gould, E. S., McCullough, J. D. (1951) J. Am. Chem Soc., 73:1109–1112.
9. Wendel, A. (1981) Methods Enzymol 77:325–333.

What is claimed is:

1. A compound having the structure:

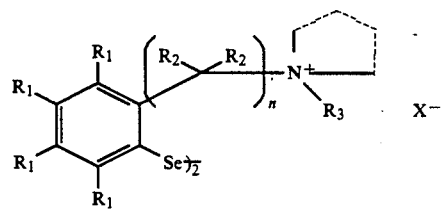

wherein n is 1;

wherein at least one $R_1$, which if more than one may be the same or different, is selected from the group consisting of $OCH_3$, $NO_2$, $CN$, $SO_3H$, $CH_2NC_4H_8$, fluoro, fluoromethyl, carboxyl, and a lower alkyl group containing one or more hydroxyl groups, and each remaining $R_1$ may be the same or different, and represents a lower alkyl group, a lower alkyl group containing one or more hydroxyl groups, or hydrogen;

wherein each $R_2$ may be the same or different and represents a lower alkyl group, a lower alkyl group containing one or more hydroxyl groups, or hydrogen;

wherein $R_3$ represents a hydrogen atom or a lower alkyl group which may be present or absent, which if present results in a positive charge on N;

wherein X is an anion which is present if $R_3$ is present and which is absent if $R_3$ is absent; and wherein the dashed lines represent carbon-carbon bonds which may be present or absent, and if absent an $N(CH_3)_2$ moiety results.

2. A compound having the structure:

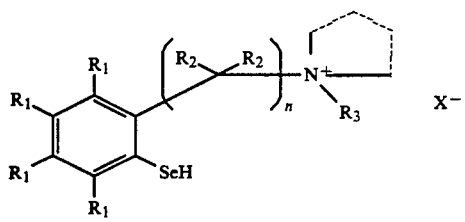

wherein n is an integer between 1 and 10;
wherein at least one $R_1$, which if more than one may be the same or different, is selected from the group consisting of $OCH_3$, $NO_2$, CN, $SO_3H$, fluoro, fluoromethyl, carboxyl, and a lower alkyl group containing one or more hydroxyl groups and each remaining $R_1$ may be the same or different, and represents a lower alkyl group, a lower alkyl group containing one or more hydroxyl groups, or hydrogen;
wherein each $R_2$ may be the same or different and represents a lower alkyl group, a lower alkyl group containing one or more hydroxyl groups, a hydroxyl group, or hydrogen, provided that both $R_2$ groups in a geminal pair are not hydroxyl;
wherein $R_3$ represents a hydrogen atom or a lower alkyl group which may be present or absent, which if present results in a positive charge on N;
wherein $X^-$ is an anion which is present if $R_3$ is present and which is absent if $R_3$ is absent; and
wherein the dashed line represent carbon-carbon bonds which may be present or absent, and if absent an $N(CH_3)_2$ moiety results.

3. A compound having the structure:

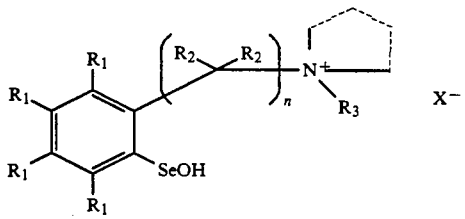

wherein n is an integer between 1 and 10;
wherein at least one $R_1$, which if more than one may be the same or different, is selected from the group consisting of $OCH_3$, $NO_2$, $SO_3H$, fluoro, fluoromethyl, carboxyl, and a lower alkyl group containing one or more hydroxyl groups, and each remaining $R_1$ may be the same or different, and represents a lower alkyl group, a lower alkyl group containing one or more hydroxyl groups, or hydrogen;
wherein each $R_2$ may be the same or different and represents a lower alkyl group, a lower alkyl group containing one or more hydroxyl groups, a hydroxyl group, or hydrogen, provided that both $R_2$ groups in a geminal pair are not hydroxyl;
wherein $R_3$ represents a hydrogen atom or a lower alkyl group which may be present or absent, and if present results in a positive charge on N;
wherein $X^{-1}$ is an anion which is present if $R_3$ is present and which is absent if $R_3$ is absent; and
wherein the dashed lines represent carbon-carbon bonds which may be present or absent, and if absent an $N(CH_3)_2$ moiety results.

4. A compound having the structure:

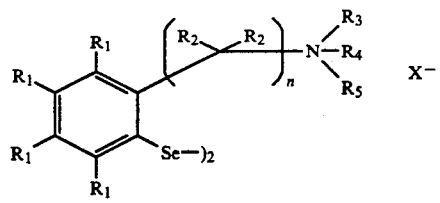

wherein n is 1;
wherein at least one $R_1$, which if more than one may be the same or different, is selected from the group consisting of $OCH_3$, $NO_2$, CN, $SO_3H$, fluoro, fluoromethyl, carboxyl, and a lower alkyl group containing one or more hydroxyl groups, and each remaining $R_1$ may be the same or different, and represents a lower alkyl group, a lower alkyl group containing one or more hydroxyl groups, or hydrogen;
wherein each $R_2$ may be the same or different and represents a lower alkyl group, a lower alkyl group containing one or more hydroxyl groups, or hydrogen;
wherein $R_3$ represents a lower alkyl group or hydrogen;
wherein $R_4$ represents a lower alkyl group or hydrogen;
wherein $R_5$ represents a hydrogen atom or a lower alkyl group which may be present or absent, and if present results in a positive charge on N; and
wherein $X^-$ is an anion which is present if $R_5$ is present and which is absent if $R_5$ is absent.

5. A compound having the structure:

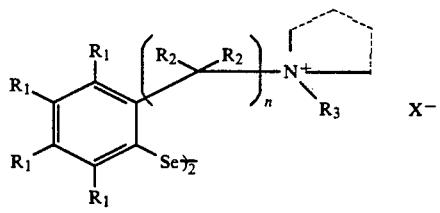

wherein n is 1;
wherein at least one $R_1$, which if more than one may be the same or different, is selected from the group consisting of $OCH_3$, $NO_2$, CN, $SO_3H$, fluoro, fluoromethyl, carboxyl, and a lower alkyl group containing one or more hydroxyl groups, and each remaining $R_1$ may be the same or different, and represents a lower alkyl group , a lower alkyl group containing one or more hydroxyl groups, hydrogen, or a free radical trapper;
wherein each $R_2$ may be the same or different and represents a lower alkyl group, a lower alkyl group containing one or more hydroxyl groups, hydrogen, or a free radical trapper;
wherein $R_3$ represents a hydrogen atom, a lower alkyl group, or a free radical trapper which may be present or absent, and if present results in a positive charge on N;

wherein X⁻ is an anion which is present if R₃ is present and which is absent if R₃ is absent; and wherein the dashed lines represent carbon-carbon bonds which may be present or absent, and if absent an N(CH₃)₂ moiety results.

6. A compound having the structure:

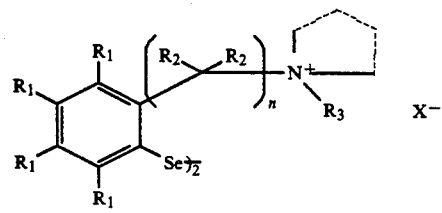

wherein n is an integer between 2 and 10;

wherein at least one R₁, which if more than one, may be the same or different, is selected from the group consisting of OCH₃, NO₂, CN, SO₃H, CH₂NC₄H₈, fluoro, fluoromethyl, carboxyl, and a lower alkyl group containing one or more hydroxyl groups, and each remaining R₁ may be the same or different, and represents a lower alkyl group, a lower alkyl group containing one or more hydroxyl groups, or hydrogen;

wherein each R₂ may be the same or different and represents a lower alkyl group, a lower alkyl group containing one or more hydroxyl groups, a hydroxyl group, or hydrogen, provided that both R₂ groups in a geminal pair are not hydroxyl;

wherein R₃ represents a hydrogen atom or a lower alkyl group which may be present or absent, and if present results in a positive charge on N;

wherein X⁻ is an anion which is present if R₃ is present and which is absent if R₃ is absent; and wherein the dashed lines represent carbon-carbon bonds which may be present or absent, and if absent an N(CH₃)₂ moiety results.

7. A compound having the structure:

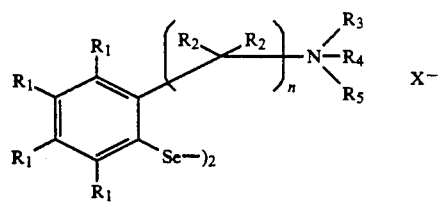

wherein n is an integer between 2 and 10;

wherein at least one R₁, which if more than one may be the same or different, is OCH₃, NO₂, CN, SO₃H, fluoro, fluoromethyl, carboxyl, and a lower alkyl group containing one or more hydroxyl groups, and each remaining R₁ may be the same or different and represents a lower alkyl group, a lower alkyl group containing one or more hydroxyl groups, or hydrogen;

wherein each R₂ may be the same or different and represents a lower alkyl group, a lower alkyl group containing one or more hydroxyl groups, a hydroxyl group, or hydrogen, provided that both R₂ groups in a geminal pair are not hydroxyl;

wherein R₃ represents a lower alkyl group or hydrogen;

wherein R₄ represents a lower alkyl group or hydrogen;

wherein R₅ represents a hydrogen atom or a lower alkyl group which may be present or absent, and if present results in a positive charge on N; and, wherein X⁻ is an anion which is present if R₅ is present and which is absent if R₅ is absent.

8. A compound having the structure:

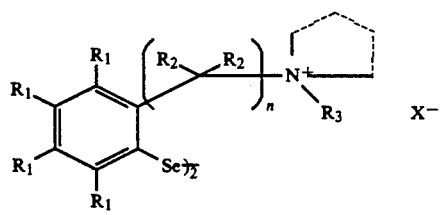

wherein n is an integer between 2 and 10;

wherein at least one R₁, which if more than one may be the same or different, is selected from the group consisting of OCH₃, NO₂, CN, SO₃H, fluoro, fluoromethyl, carboxyl, and a lower alkyl group containing one or more hydroxyl groups, and each remaining R₁ may be the same or different, and represents a lower alkyl group, a lower alkyl group containing one or more hydroxyl groups, hydrogen, or a free radical trapper;

wherein each R₂ may be the same or different and represents a lower alkyl group, a lower alkyl group containing one or more hydroxyl groups, a hydroxyl group, hydrogen, or a free radical trapper, provided that both R₂ groups in a geminal pair are not hydroxyl;

wherein R₃ represents a hydrogen atom, a lower alkyl group, or a free radical trapper which may be present or absent, and if present results in a positive charge on N;

wherein X⁻ is an anion which is present if R₃ is present and which is absent if R₃ is absent; and wherein the dashed lines represent carbon-carbon bonds which may be present or absent, and if absent an N(CH₃)₂ moiety results.

9. A compound of claim 2, 3, or 6, wherein n is between 2 to 6.

10. A compound of claim 1 or 6, wherein one or more R₁ are thiols.

11. A compound of claim 1 or 6 wherein one or more R₁ are —SH or —S—CH₃.

12. A compound of claim 2 having the structure:

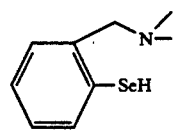

13. A compound of claim 4 or 7, wherein n is between 2 to 6.

14. A compound of claim 4 or 7, wherein one or more R₁ are thiols.

15. A compound of claim 4 or 7, wherein one or more R₁ are —SH or —S—CH₃.

16. A pharmaceutical composition which comprises an amount of a compound of claim 1, 4, 6, or 7, effective to reduce H₂O₂ and/or other peroxides in a subject afflicted with a peroxide-induced condition and a pharmaceutically acceptable carrier.

17. A pharmaceutical composition of claim 16, wherein the pharmaceutical composition further comprises a cofactor.

18. A pharmaceutical composition of claim 17, wherein the cofactor is ascorbic acid, glutathione, cysteine, cystamine, dithiothreitol, or mercaptoethanol.

19. A compound of claim 1 or 6, wherein one or more $R_1$ are nitro groups, fluoro groups, fluoromethyl groups, or carboxyl groups.

20. A compound of claim 19 having the structure:

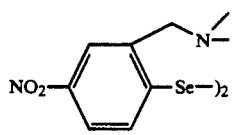

21. A compound of claim 1 or 6, wherein one or more $R_1$ are —$CH_2NC_4H_8$.

22. A compound of claim 21 having the structure:

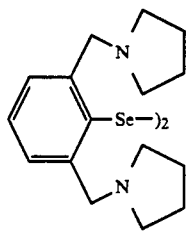

23. A composition comprising an amount of a compound of claim 1 or 6 and an amount of a free-radical trapper.

24. A compound of claims 5 or 8, wherein the free radical trapper is 2,2,6,6-tetramethylpiperidine-1-oxyl.

25. A compound of claims 5 or 8, wherein the free radical trapper is 2,2,5,5-tetramethyl-3-pyrroline-1-oxyl-3-carboxylic acid.

26. A compound of claim 24 having the structure:

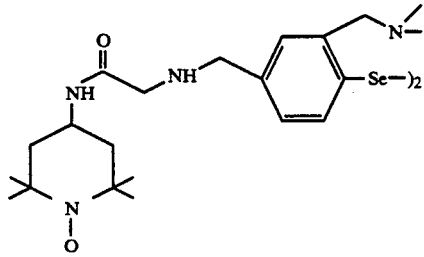

27. A compound of claim 25 having the structure:

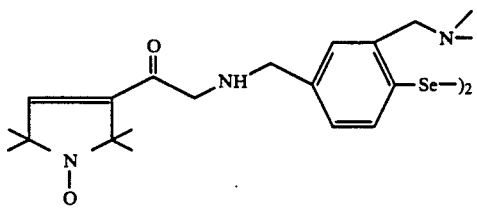

* * * * *